US008808249B2

(12) United States Patent
Langan et al.

(10) Patent No.: US 8,808,249 B2
(45) Date of Patent: Aug. 19, 2014

(54) INTRAVENOUS BAG/LINE SAFETY DEVICE

(71) Applicant: PharMEDium Services, LLC, Lake Forest, IL (US)

(72) Inventors: Amy Elizabeth Langan, Chicago, IL (US); Karen Pinderski, Lake Forest, IL (US); Patricia Lynn Miyake, Mundelein, IL (US); Kenneth G. Oswald, Arlington Heights, IL (US); Thomas Edward Cosentino, Gurnee, IL (US); Richard John Kruzynski, Long Grove, IL (US)

(73) Assignee: PharMEDium Services, LLC, Lake Forest, IL (US)

( * ) Notice: Subject to any disclaimer, the term of this patent is extended or adjusted under 35 U.S.C. 154(b) by 0 days.

(21) Appl. No.: 14/093,765

(22) Filed: Dec. 2, 2013

(65) Prior Publication Data

US 2014/0090226 A1  Apr. 3, 2014

Related U.S. Application Data

(63) Continuation of application No. 13/926,759, filed on Jun. 25, 2013, now Pat. No. 8,597,271, which is a continuation of application No. 13/743,981, filed on Jan. 17, 2013.

(60) Provisional application No. 61/587,207, filed on Jan. 17, 2012.

(51) Int. Cl.
*A61M 3/00* (2006.01)
*A61J 1/14* (2006.01)
*A61M 5/14* (2006.01)
*G09F 3/10* (2006.01)
*A61J 1/10* (2006.01)

(52) U.S. Cl.
CPC ............ *A61J 1/1462* (2013.01); *A61M 5/1417* (2013.01); *G09F 3/10* (2013.01); *A61J 1/10* (2013.01)
USPC ......................................................... 604/189

(58) Field of Classification Search
CPC ....... A61J 1/10; A61J 2205/30; B65D 23/005
USPC .................................................. 604/404, 189
See application file for complete search history.

(56) References Cited

U.S. PATENT DOCUMENTS

| | | |
|---|---|---|
| 4,526,404 A | 7/1985 | Vazquez |
| 5,782,495 A * | 7/1998 | Grosskopf et al. .............. 283/81 |
| 5,799,981 A | 9/1998 | Tung et al. |

(Continued)

OTHER PUBLICATIONS

"I.V. ID Labels", product brochure from www.rollproducts.com, downloaded Jul. 23, 2013, Roll Products, Inc. St. Marys, KS, 1 page.

*Primary Examiner* — Kevin C Sirmons
*Assistant Examiner* — Deanna K Hall
(74) *Attorney, Agent, or Firm* — Drinker Biddle & Reath LLP

(57) ABSTRACT

An IV bag/line safety device including a tag set and a bag attacher removably connected to the tag set. The tag set includes a plurality of tags printed with the name of an IV solution. The bag attacher is configured to attach the safety device to an IV bag containing the IV solution printed on the tags. After attachment, the safety device provides visual cues to a user inviting the user to disconnect the tags from the safety device. After disconnecting one or more of the tags, the user may attach those tags to an IV tubing line connected to the IV bag through which the IV solution contained in the IV bag flows from the IV bag into a patient. This enables the user to quickly identify a given IV tubing line having at least one tag attached thereto as containing a particular IV solution.

19 Claims, 20 Drawing Sheets

(56) References Cited

U.S. PATENT DOCUMENTS

| | | | |
|---|---|---|---|
| 5,855,395 A | 1/1999 | Foote et al. |
| 6,035,568 A | 3/2000 | Grosskopf et al. |
| 2002/0056989 A1 | 5/2002 | Lewis-Leander |
| 2013/0289496 A1 | 10/2013 | Langan et al. |

* cited by examiner

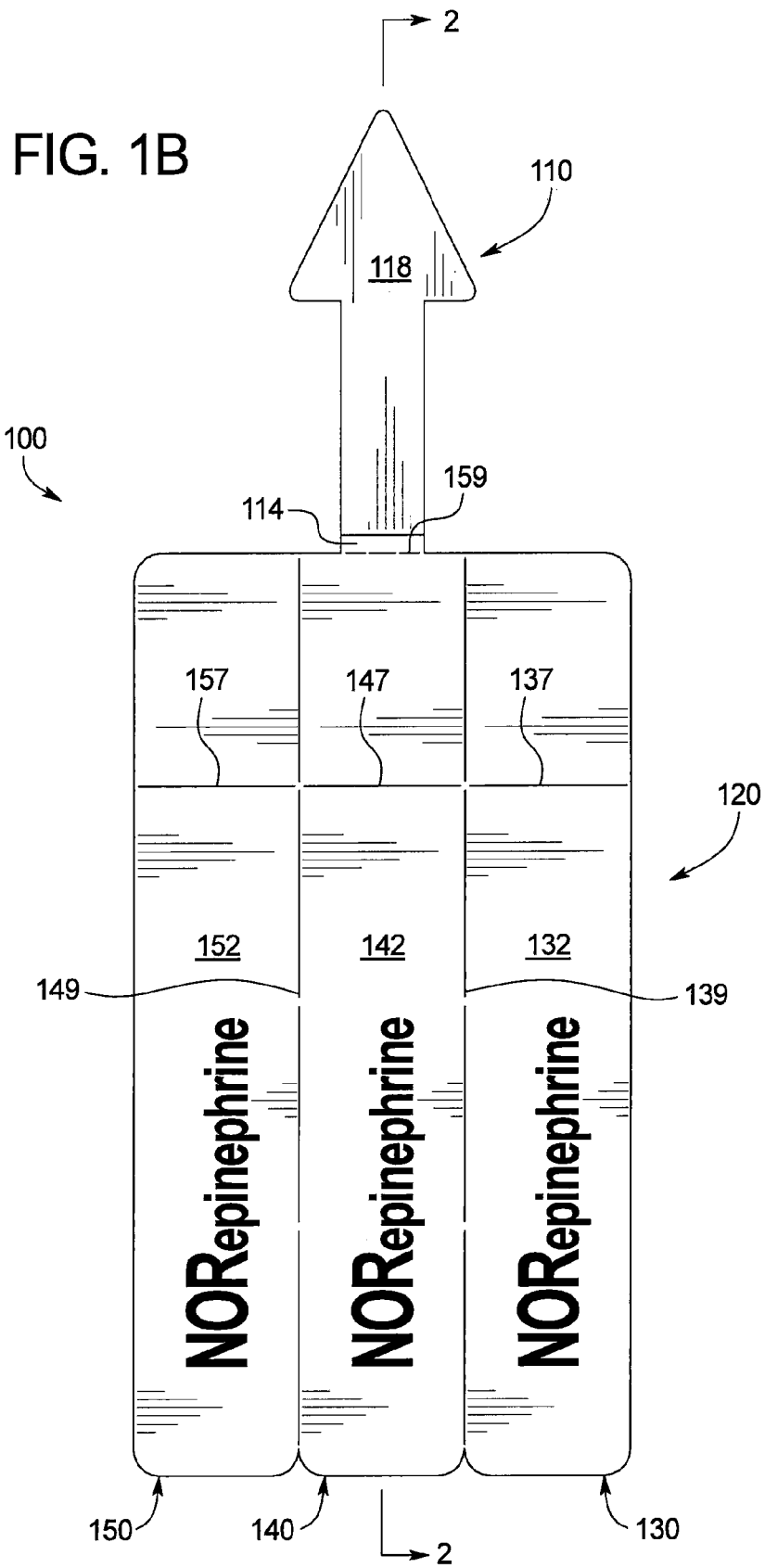

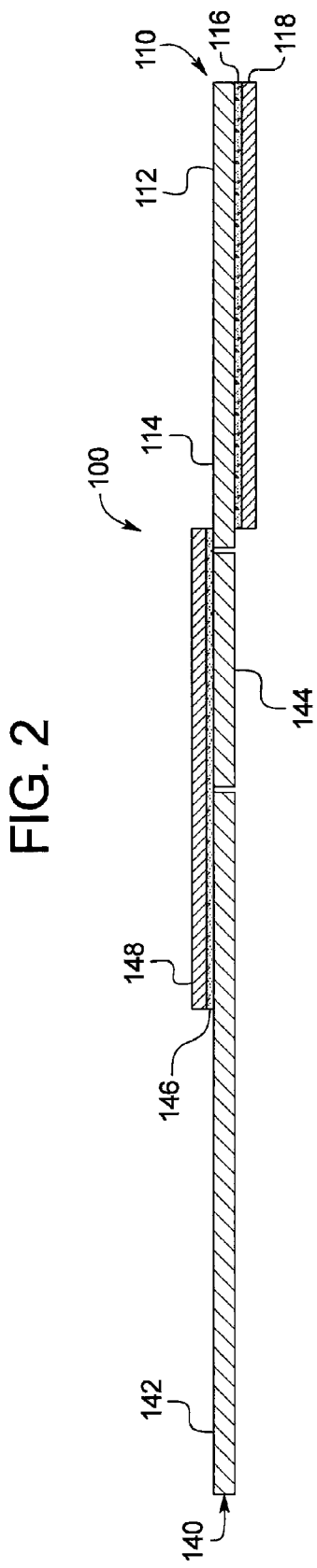

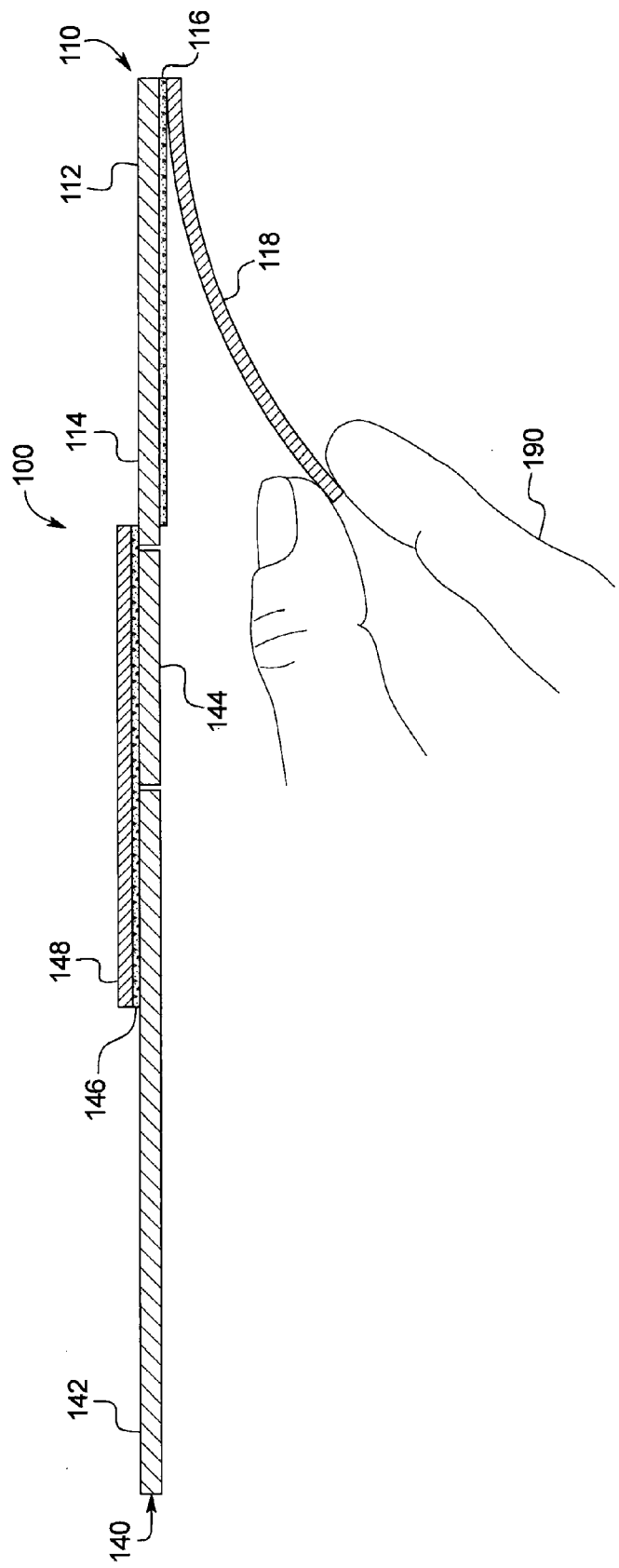

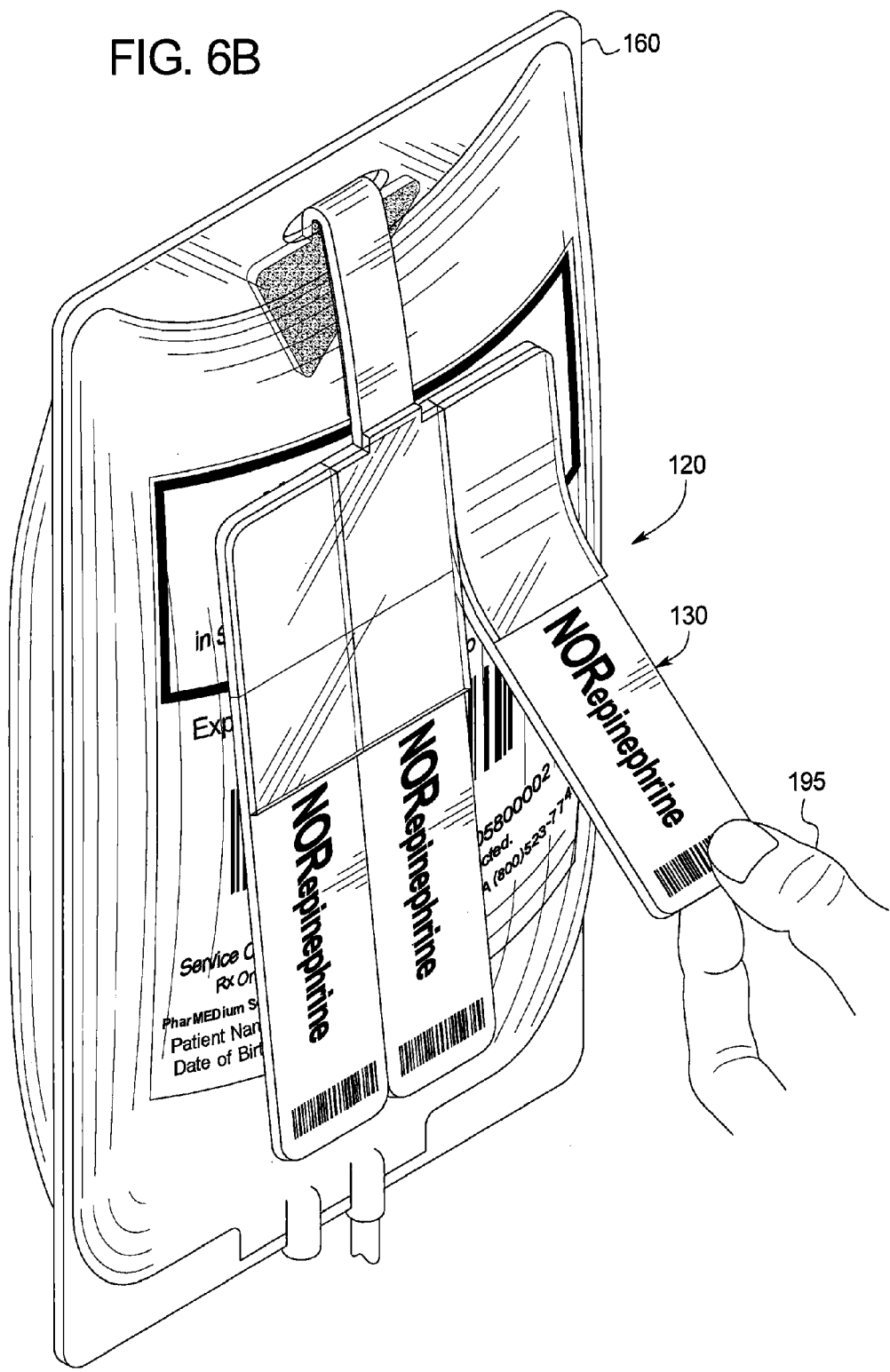

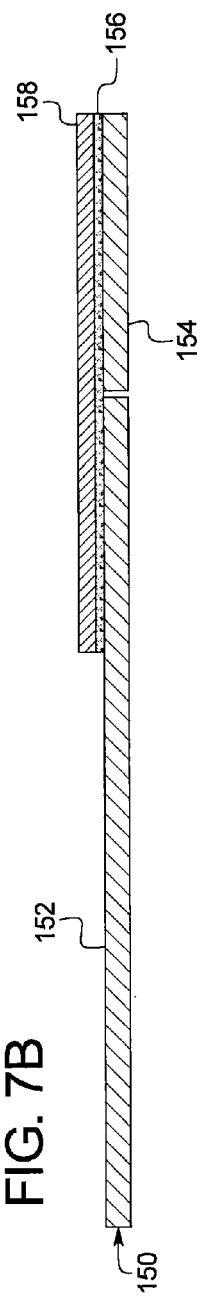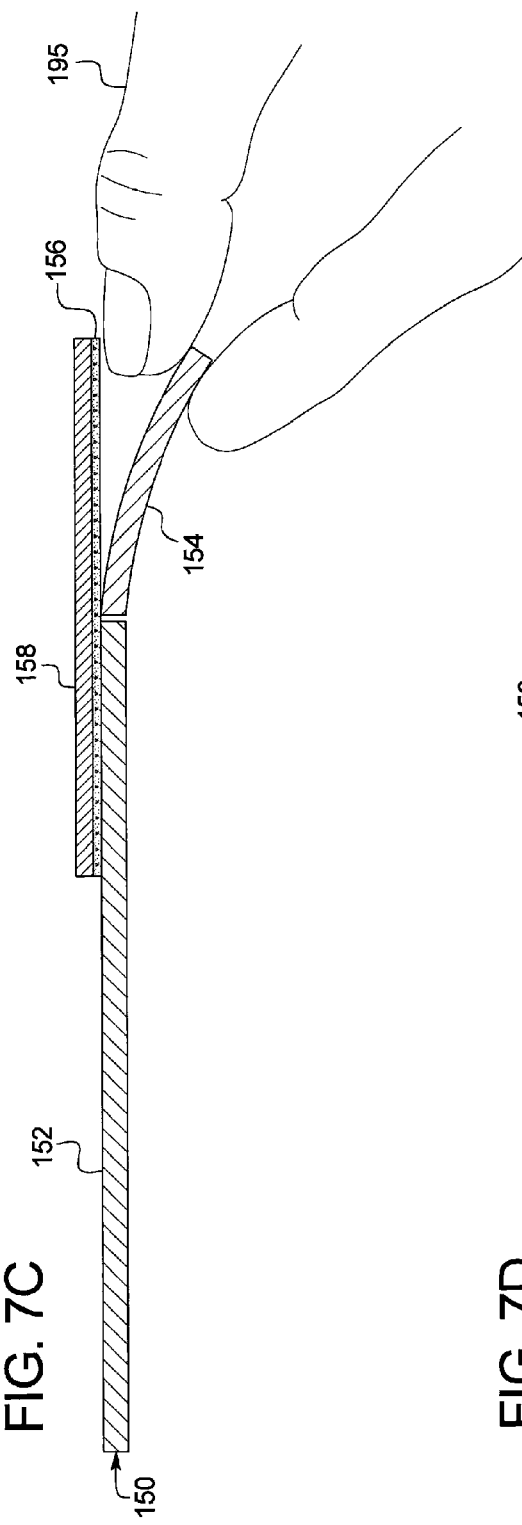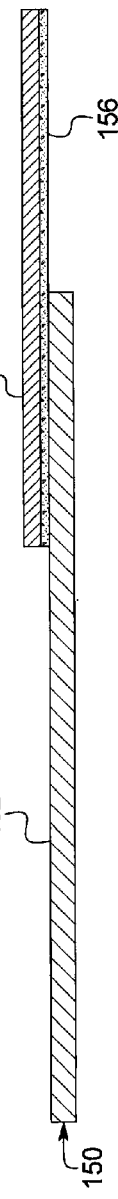

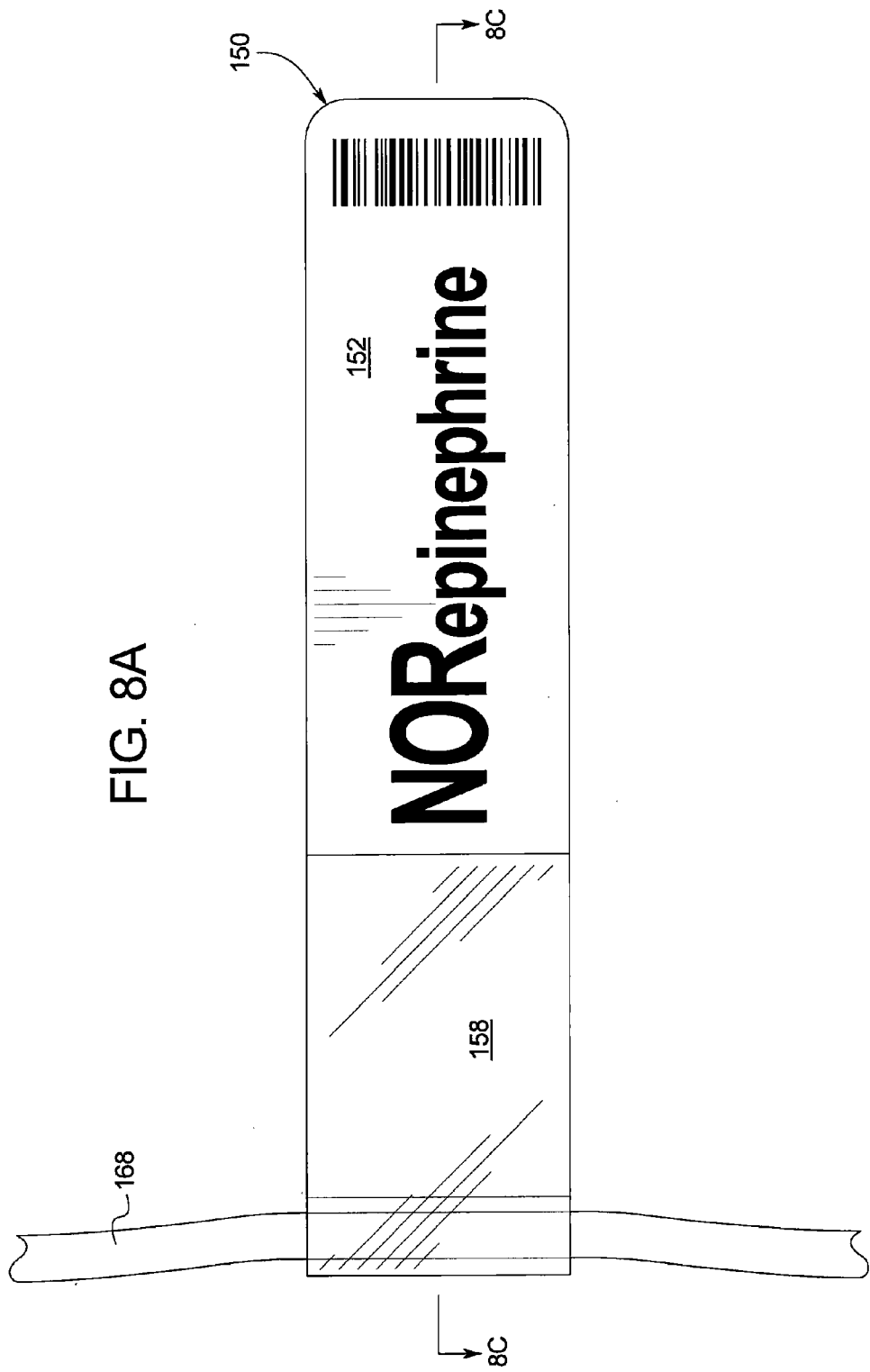

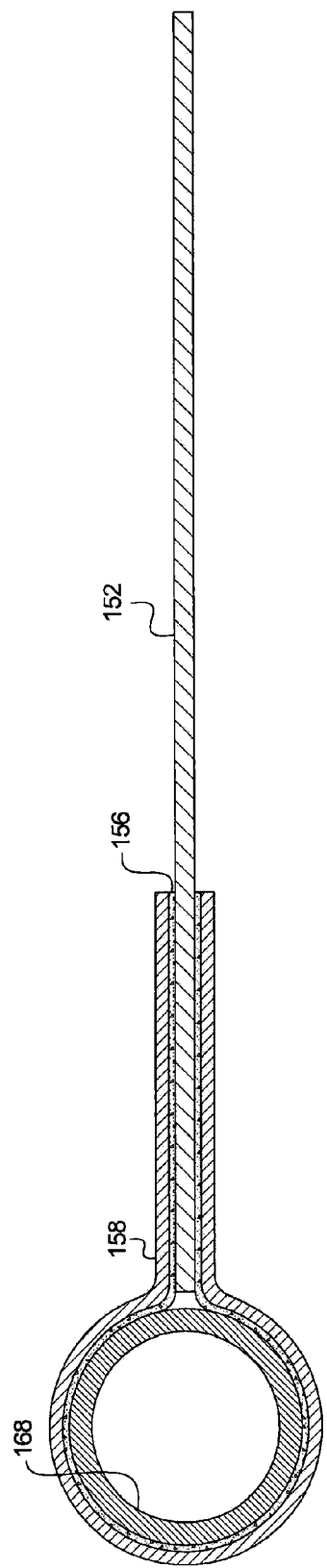

INTRAVENOUS BAG/LINE SAFETY DEVICE

PRIORITY CLAIM

This application is a continuation of U.S. patent application Ser. No. 13/926,759 filed Jun. 25, 2013, which is a continuation of U.S. patent application Ser. No. 13/743,981 filed Jan. 17, 2013, which claims priority to U.S. provisional patent application No. 61/587,207 filed Jan. 17, 2012, all of which are incorporated herein by reference in their entirety.

COPYRIGHT NOTICE

A portion of the disclosure of this patent document contains or may contain material that is subject to copyright protection. The copyright owner has no objection to the photocopy reproduction by anyone of the patent document or the patent disclosure in exactly the form it appears in the Patent and Trademark Office patent file or records, but otherwise reserves all copyright rights whatsoever.

BACKGROUND

Various health care providers, such as anesthesiologists, anesthesiologist's assistants, medical doctors, nurses, and nurse's assistants, administer liquid pharmaceuticals and liquid nutrients to patients in a variety of different medical settings, such as in an intensive care unit (ICU), a critical care unit (CCU), an intensive treatment unit (ITU), a high dependency unit (HDU), an emergency room (ER), and the like. Health care providers also administer liquid pharmaceuticals and liquid nutrients to patients during a variety of medical procedures, such as, but not limited to, during surgery in an operating room or in an ICU. Health care providers may administer the liquid pharmaceuticals and liquid nutrients in a variety of different manners, such as: intravenously, such as through a central venous catheter (or central line); via an epidural; or via a subcutaneous injection.

To administer a liquid pharmaceutical and liquid nutrients to a patient intravenously, a health care provider often utilizes an intravenous (IV) bag containing that liquid pharmaceutical and those liquid nutrients, which are normally suspended in a carrying liquid or carrier (together referred to herein as the 'intravenous (IV) solution' for brevity). The IV bag typically has one or more permanent labels attached to the front and/or back surfaces of the bag that identify the IV solution contained in that IV bag. The permanent labels also include additional information about that IV solution, such as (but not limited to) the concentration of the pharmaceutical contained therein, the class of the pharmaceutical contained therein, and/or dosage guidelines of the pharmaceutical contained therein. The health care provider typically hangs the IV bag on an IV bag stand (such as an IV bag holder pole) located in close proximity to the patient (or in close proximity to the bed of the patient), and typically connects an IV tubing line connected to and extending from the IV bag to the patient in one of the variety of different manners mentioned above. After the IV bag is connected to the patient via the IV tubing line, the health care provider typically uses a drip chamber, a clamp, and/or an IV administration manifold system to control the flow of the IV solution into the patient.

In certain settings, such as in an ICU that houses a hospital's most critical patients, a typical patient is often simultaneously administered multiple different IV solutions intravenously at any given time. Typically, an ICU patient is administered between three and eighteen different IV solutions intravenously at any given time. It should be appreciated, however, that any suitable number of different IV solutions, such as three, five, ten, fifteen, twenty, or more different IV solutions, may be administered to a patient at any one time during treatment. Each of the IV solutions is usually contained in a different IV bag, and each of the IV bags is connected to a separate IV tubing line that, in turn, is connected to the patient. Thus, a typical ICU patient could have anywhere from three to eighteen (or more) IV tubing lines each running from a different IV bag to the patient. The number of IV bags connected to a patient may vary during the patient's stay in the ICU. For example, as the patient heals, the number of IV bags connected to the patient (i.e., the number of different IV solutions the patient needs) decreases. Since the IV bags are hung in close proximity to the patient on one or more IV bag stands, and thus in close proximity to one another, the IV tubing lines can intersperse with one another, often times resulting in a jumbled, tangled web of IV tubing lines, all of which are typically substantially similar in appearance.

This tangled web of similar IV tubing lines appears chaotic when compared to the otherwise orderly ICU. Specifically, since the ICU houses the hospital's most critical patients, the ICU is, by necessity, an extremely controlled environment. The strictly controlled ICU environment creates a relaxed or stress-reduced atmosphere or environment for the ICU patients, who are normally trying to recover from major accidents, major surgery, or other considerable ailments or health issues. To create such an atmosphere or environment, ICUs typically employ dim lighting relative to the standard harsh or bright fluorescent hospital lighting, and minimize noise by, for example, restricting visiting hours and restricting or eliminating the use of televisions.

While the ICU environment is strictly controlled in an attempt to reduce stress on patients, it is also strictly controlled to reduce the stress on ICU nurses and other health care providers. The critical nature of the patients housed in an ICU creates a stressful, complex, and chaotic environment in which the health care providers work. For example, health care providers must be ready and able to attend to any medical emergencies, which are likely to occur relatively frequently in the ICU due to the critical nature of the patients. To reduce this chaos and complexity, ICUs are extremely organized and ICU nurses are trained to keep the ICU as clutter free as possible. For example, medical instruments and other supplies are housed in certain specific locations, known to the health care providers, which enable them to perform both routine and emergency medical procedures and other tasks quickly and efficiently. This reduces the potential for complications to arise when medical procedures are performed in the ICU, such as by reducing the items that need to be regularly cleaned to prevent inventions from lingering bacteria.

The chaos created by the tangled web of IV tubing lines combined with the environment of the ICU makes working with the IV bags and IV tubing lines difficult or stressful for ICU nurses or other health care professionals. For instance, the nurse or nurses often must spend time untangling the IV tubing lines to determine which IV tubing line belongs to which IV bag when, for example, one or more of those IV bags needs to be changed. Since a patient connected to a large number of IV bags may need one or more of the IV bags changed at various times throughout each day, the nurse or nurses must perform this process several times every day. This is more problematic in emergency situations when time is of the essence. If, during a patient emergency, an IV bag must be disconnected or replaced, the nurse or nurses must wade through the web of IV tubing lines to ensure the nurse or nurses are removing the correct IV bag. This problem is worsened by the fact that the IV bags are hung in close proximity to one another, making it difficult for the nurse or nurses to read the permanent labels on the IV bags to differentiate the IV bags from one another and identify the IV solutions contained in those bags. The fact that the lighting in the ICU is dim and that the nurse or nurses must try to work quietly so as not to disturb or stress other patients further complicates these tasks.

The combination of these issues may lead to a nurse's failure to correctly identify an IV bag as containing a particular pharmaceutical, which could cause significant problems and complications for the patient. For example, if a certain IV bag containing an IV solution vital to a patient's stability (or possibly livelihood) is accidentally disconnected from the patient (because the nurse removes the wrong IV tubing line), the patient could suffer severe complications, setbacks to recovery, or even death. Even if the mistake is quickly realized, another IV bag must be connected, which can cause additional stress to an already fragile patient. Additionally, each time an IV bag is connected or unconnected to a patient, there is a risk of infection or other danger such as an air bubble entering the IV tubing line and, eventually, the patient. Unnecessary disconnections and reconnections of IV bags vastly increase these risks.

At least three known solutions that attempt to remedy these problems have been proposed, but each either fails to solve these problems and/or creates new problems.

U.S. Patent Application Publication No. 2002/0056989 to Lewis-Leander proposes one solution to these problems. Specifically, Lewis-Leander proposes affixing a main (i.e., permanent) label having a plurality of detachable labels to an IV bag. One entire side of each detachable label is printed with a single instance of the name of the IV solution contained in the IV bag. The other side of each detachable label includes an adhesive. After the main label is affixed to an IV bag, a user may remove one of the detachable labels by tearing it from the main label, and attach the detachable label to an IV tubing line connected to the IV bag by wrapping the detachable label around the IV tubing line such that the adhesive affixes the detachable label to the IV tubing line.

The Lewis-Leander proposed solution causes at least five additional problems. The first additional problem is that users, such as nurses or other health care providers, are reluctant to remove a portion of a permanent label on an IV bag. Nurses are trained not to destroy or alter permanent labels on IV bags because those permanent labels include vital information that may be critical to a patient's health and safety, and asking nurses to do so would contradict this training. Second, even if a nurse was willing to remove part of a permanent label on the IV bag, the permanent label on the IV bag can be damaged through the use of the Lewis-Leander proposed solution. For example, since the detachable labels must be torn off of the main label itself to be used (i.e., attached to the IV tubing line), it is possible that certain portions of the main label, and thus certain vital information, may be torn off of the main label along with the detachable labels, thereby rendering this information unavailable to the nurse.

The third additional problem created by the Lewis-Leander proposed solution is that it is difficult for a nurse to remove the detachable labels from the main label. As explained above, the main label is affixed to the IV bag, meaning that the detachable labels are positioned in close proximity to the IV bag. Due to the positioning of the main label and the detachable labels, the nurse must handle and manipulate the IV bag, which is full of an IV solution, to remove one or more of the detachable labels. This additional handling and manipulation of the IV bag increases the possibility that the IV bag will be ripped, punctured, or otherwise contaminated and rendered useless during the process of removing the detachable labels from the main label.

The fourth additional problem is that the Lewis-Leander proposed detachable labels do not provide the health care provider any cues, visual or otherwise, to remove the detachable labels from the main label. Since the detachable labels are attached to the main label and, therefore, positioned in close proximity to the IV bag, it appears upon first glance that the detachable labels are simply part of the main label and used to identify the IV bag itself as containing the IV solution. There is nothing that prompts the nurse to reach out and detach one or more of the Lewis-Leander detachable labels. The fifth additional problem created by the Lewis-Leander proposed solution stems from the fact that the detachable labels are opaque. When these opaque detachable labels are wrapped around an IV tubing line, the nurse is not able to view the IV solution flowing through that section of the IV tubing line. This is problematic because the nurse will not be able to see whether there are any issues within that section of the IV tubing line, such as a blockage.

In addition, the Lewis-Leander proposed solution does not solve all of the problems explained above that stem from the tangled web of IV tubing lines. Specifically, since each detachable label includes a single instance of an IV solution name (or the name of the pharmaceutical therein) printed across the entirety of only one side of that detachable label, when that detachable label is wrapped around an IV tube, the entire IV solution name is not visible or readily readable unless the nurse manipulates and repositions the detachable label (to read the entire name). That is, the use of the Lewis-Leander proposed solution would still require a nurse to handle and manipulate the IV tubing lines (with the detachable label or labels attached thereto) to determine which tubing line contains which IV solution. It is likely for this reason, and because of the five additional problems discussed above, that the Lewis-Leander proposed solution has not been commercially implemented.

System One Medical provides another proposed solution in the form of a roll of opaque labels. One side of each label includes an adhesive covered by a liner, and the other side includes a blank space in which the name of an IV solution may be written by a nurse (or other health care provider) or printed using a thermal printer. Prior to attaching one of the labels to an IV tubing line, the nurse must write on the blank label the name of the IV solution (or the name of the pharmaceutical therein) in an IV bag to which the IV tubing line is connected. The nurse then removes the liner and uses the adhesive to attach that label to the IV tubing line by wrapping the adhesive portion of the label around the IV tubing line. The System One Medical proposed solution fails to remedy the fourth and fifth problems inherent in the Lewis-Leander proposed solution discussed above. Specifically, the labels of the System One Medical proposed solution are also opaque, and since the labels of the System One Medical proposed solution are not initially attached to any IV bags, they do not provide any visual cues to the nurse to use the labels. That is, when the nurse views the IV bag, such as when the nurse initially sets up the IV bag, there are no cues that remind the nurse to utilize the labels.

Additionally, the labels of the System One Medical proposed solution require the nurse to take multiple additional steps and use multiple additional tools and materials during preparation of an IV bag and its corresponding IV tubing line. Namely, the System One Medical proposed solution requires the nurse to locate the roll of blank labels, write out the name of an IV solution on the label using a pen, detach the label from the roll, and attach the label to the IV tubing line. These additional steps are inconvenient, especially when the nurse is pressed for time in an emergency, and may deter the use of the labels. Further, the fact that the nurse must write the IV solution name on the label introduces the possibility of human error if, for example, the nurse writes the incorrect IV solution name, misspells the IV solution name, or writes a confusing abbreviation of the IV solution name. Also, certain nurses may not be able to read the handwriting of other nurses, or the ink used to write on the labels may smear or bleed. That is, the System One Medical labels are not waterproof. Further, the labels of the System One Medical proposed solution are not rigid, and may curl or otherwise deform after attachment, making it difficult for the nurse or nurses to read the IV solution name written on the tag. More specifically, at times, nurses monitor ICU patients by watching the patients through glass monitoring windows in the ICU. This enables nurses to determine whether a patient's IV bag is low or empty without having to enter the ICU and disturb the patient or any of the other patients. Since the System One Medical labels are not rigid and may curl, the nurses may not be able to view the labels through the monitoring windows and identify the IV solution in the low or empty IV bags. The nurse would have to enter the ICU to make that determination, potentially disturbing patients.

Another proposed solution that is somewhat utilized involves a nurse or nurses using a piece of a roll of tape to identify IV tubing lines. To identify an IV tubing line in this manner, a nurse: (a) locates a roll of white cloth, paper, or plastic medical tape; (b) uses scissors to cut a piece of tape from the roll or tears a piece of tape from the roll; (c) uses a pen to write the name of an IV solution on the piece of tape; and (d) wraps the piece of tape around an IV tubing line connected to an IV bag containing that IV solution. Nurses often do this two or three times to attach pieces of tape to multiple spaced apart spots on each IV tubing line. The medical tape proposed solution suffers from the same problems as the System One Medical proposed solution. Namely, the medical tape proposed solution involves using opaque tape and provides no visual cues to the nurse to use the tape in such a manner. Also, the tape is not rigid, and may deform or curl, making reading the written IV solution name difficult. This could also cause nurses to not be able to read the written IV solution name through an ICU monitoring window, as described above. The possibility for human error is high in this system is well. For example, nurses may write the incorrect IV solution name, nurses may not be able to read one another's handwriting, and nurses may use abbreviations of IV solution names that are confusing or unrecognizable to others. Further, there is a possibility that the ink used in the medical tape proposed solution could bleed or smear (similar to the System One Medical labels). Additionally, the adhesive on the tape is not medical grade adhesive, and may leach through the IV tubing line and make its way into the IV solution. Thus, the medical tape proposed solution increases the risk that the IV solution could become contaminated while being administered to the patient.

Additionally, the medical tape proposed solution requires a considerable amount of time and effort and, like the System One Medical proposed solution, requires additional materials, such as a pen, tape, and scissors. The medical tape proposed solution thus diverts a nurse's attention away from the critical patients while they spend time preparing a number of pieces of tape. The additional materials required also clutter the ICU, and provide more surfaces for bacteria and other infectious agents to grow, thereby exposing the patients to possible infection and possibly contaminating the otherwise clean ICU environment.

Accordingly, there is a substantial need to provide an IV bag/line safety device that does not interfere with permanent labeling on IV bags, that is easy to use, that provides cues that remind a health care professional to use the safely device, that requires minimal additional work on the part of the health care professional, that maintains or increases patient safety, that aids in maintaining the environment of the ICU, and that reduces the potential for human error.

SUMMARY

Various embodiments of the present disclosure provide an intravenous (IV) bag/line safety device. The IV bag/line safety device of the present disclosure is sometimes referred to herein as the safety device for brevity.

In various embodiments, the safety device includes a tag set and a bag attacher removably connected to the tag set. The tag set includes one or more IV tubing line safety tags. In one embodiment, the tag set includes three IV tubing line safety tags and, in particular, a first IV tubing line safety tag, a second IV tubing line safety tag, and a third IV tubing line safety tag. The first tag is removably connected to the second tag via a first perforated edge, the third tag is removably connected to the second tag via a second perforated edge, and the second tag is removably connected to the bag attacher via a third perforated edge.

In various embodiments, each of the tags includes an IV solution name displayer removably connected to an IV tubing line adhesive protective cover via a perforated edge, and an IV tubing line attacher having an IV tubing line adhesive disposed on and adhering to the back surface of the IV tubing line attacher. For each of the tags, a portion of the IV solution name displayer is attached to the IV tubing line adhesive, and all or substantially all of the IV tubing line adhesive protective cover is removably attached to the IV tubing line adhesive. A name of an IV solution (such as a name of the pharmaceutical therein) is printed or otherwise formed on both the front and back surfaces of each of the IV solution name displayers of the tags.

In various embodiments, the bag attacher includes a head, a neck connected at one end to the head, a bag attacher adhesive disposed on and adhering to one surface of the head and the neck, and a bag attacher adhesive protective liner removably attached to and covering the bag attacher adhesive.

In various embodiments, the IV bag/line safety device disclosed herein and, more specifically, the bag attacher, may be attached to an IV bag (and thus prepared for use) by any suitable bag preparer prior to delivery to a hospital or other medical facility. Typically, one or more manufacturers manufacture the IV bag and the IV tubing line. Subsequent to manufacturing, the IV bag and the IV tubing line are wrapped in one or more sealed outer bags and sterilized. After sterilization, the interior and the exterior of the IV bag and the interior and the exterior of the IV tubing line (which are contained within one or more outer bags) are sterile. After sterilization, the outer bag or bags (containing the IV bag and/or the IV tubing line) are delivered to an IV bag filler, such as a pharmacy or a pharmacy compounder (such as the assignee of this application). The IV bag filler fills the IV bag with an IV solution, i.e., with a liquid pharmaceutical and/or liquid nutrients suspended in a carrying liquid. It should be appreciated that, in certain instances, one IV bag filler fills the IV bag with a liquid pharmaceutical and/or liquid nutrients and another, different IV bag filler fills the IV bag with a carrying liquid. Before or after filling, an IV bag label attacher attaches one or more permanent labels to the IV bag identifying the solution (or the name of the pharmaceutical therein) contained by (or that will be contained by) the IV bag. After filling, the (filled) IV bag and the IV tubing line are wrapped in a sealed outer bag. It should be appreciated that after filling the interior of the IV bag remains sterile. The wrapped IV bag and IV tubing line are then delivered to a hospital or other medical facility. Upon receipt, a pharmacist (or other health care provider) catalogs the IV bag and stores it for future use by hospital staff, such as a health care provider in an ICU.

It should be appreciated that, in various embodiments, the IV bag/line safety device of the present disclosure may be attached to the IV bag at any suitable point during the above process. That is, the IV bag/line safety device may be attached to the IV bag at any one of a variety of different times during the process and before a health care provider, such as a nurse working in an ICU, retrieves the IV bag for use with a patient. For example, in certain embodiments, the manufacturer of the IV bag attaches the IV bag/line safety device to the IV bag before sterilization. It should be appreciated that, in these embodiments, the IV bag/line safety device is sterilized along with the IV bag and/or the IV tubing line prior to delivery to an IV bag filler. In other embodiments, the IV bag filler attaches the IV bag/safety device to the IV bag after sterilization. That is, in these embodiments, upon receipt of the sterilized IV bag from the IV bag manufacturer, the IV bag filler removes the outer wrapping and attaches the IV bag/line safety device to the IV bag. It should be appreciated that, in these embodiments, the IV bag/line safety device is itself sterilized prior to being attached to the IV bag. In certain other embodiments, the IV bag/line safety device is attached to the IV bag by the pharmacist (or another health care provider) at the hospital or other medical facility after receipt from the IV bag filler. That is, in these embodiments, neither the IV bag manufacturer nor the IV bag filler attaches the IV bag/line safety device to the IV bag. It should also be appreciated that, in these embodiments, the IV bag/line safety device is itself sterilized prior to being attached to the IV bag.

To attach the safety device to the IV bag, a bag preparer: (a) removes the bag attacher adhesive liner from the bag attacher, thereby exposing the bag attacher adhesive; (b) inserts the head through the hanger hole of the IV bag; (c) folds the head over near the junction of the head and the neck; and (d) presses the head against the back surface of the IV bag and presses the neck against the front surface of the IV bag such that the bag attacher adhesive adheres to the front and back surfaces of the IV bag, thereby attaching the head; the neck; and, necessarily, the bag attacher and the safety device as a whole to the IV bag.

After attachment to the IV bag, the safety device provides visual cues to a user, such as a nurse working in an ICU, that readily invite the user to detach the tag set, as a whole, from the bag attacher, or to detach one or more of the tags. Specifically, after attachment the tag set hangs or dangles off of the IV bag (similar to the way in which a price tag hangs off of a piece of clothing). The fact that the tag set itself is not attached to, and is loosely hanging or dangling from, the IV bag over the permanent label (and not as part of the permanent label) cues the user to detach the tag set as a whole from the bag attacher or to detach one or more of the tags (similar to how one would detach a price tag from a recently-purchased item of clothing before using the clothing). Upon viewing the dangling tags, the nurse (or other user) will intuitively want to remove them; that is, the hanging or dangling tags clearly convey to the nurse that they are removable and should be removed. When the safety device of various embodiments of the present disclosure is initially attached to the IV bag, the tag set may block all or a portion of one of the permanent labels on the IV bag. The fact that the user may not be able to read all or part of that permanent label also cues the user to detach the tag set from the bag attacher. In other words, the use of the safety device in some ways requires the user to remove the tags to properly read the permanent label on the IV bag.

After detaching one or more of the tags, the user may attach those tags to an IV tubing line connected to the IV bag through which the IV solution contained in the IV bag flows from the IV bag into a patient. The user does so by peeling the IV tubing line adhesive protective cover from the IV tubing line adhesive, and wrapping the IV tubing line attacher around the IV tubing line such that the IV tubing line adhesive adheres the tag to the IV tubing line. Since the name of the IV solution (or the name of the pharmaceutical) printed on the tags is the IV solution contained in the IV bag (or the name of the pharmaceutical) to which the safety device is attached, the tags identify the IV tubing line to which they are attached as containing the IV solution in the IV bag. This enables the user to quickly and easily identify which IV solution a given IV tubing line (having one of more of the tags attached thereto) contains.

After attachment to the IV bag, the safety device of the present disclosure enables a user to quickly, easily, safely, and conveniently identify an IV tubing line of an IV bag, thereby assisting the user in making sense of what would otherwise be a tangled web of IV tubing lines, and does so while avoiding the additional problems created by the three proposed solutions discussed above. First, the safety device of the present disclosure is in addition to any permanent labels on the IV bags, meaning that users do not have to worry about altering the permanent labels or tearing off portions of the permanent labels (and potentially damaging them). Second, the safety device of the present disclosure features tags that are readily and easily detachable from the safety device. Third, as described in detail above, the safety device of the present disclosure provides visual cues that cue the user to remove and use the tags. Fourth, the IV tubing line attacher and the IV tubing line adhesive of the safety device of the present disclosure are transparent or substantially transparent. Once a tag is attached to an IV tubing line, a user will be able to see through the IV tubing line attacher and the IV tubing line adhesive and view the IV solution flowing through the IV tubing line.

Fifth, the safety device of the present disclosure includes tags that have a designated amount of rigidity so that they maintain their shape and orientation after attachment to an IV tubing line. The fact that the tags maintain their shape makes it relatively easy for nurses or other health care professionals to read the tags through a monitoring window in an ICU. Sixth, the safety device of the present disclosure includes tags that are pre-printed on both sides with a complete IV solution name and that are pre-attached to an IV bag containing that IV solution. Thus, the safety device of the present disclosure does not require users to write the name of the IV solution or a confusing abbreviation thereof, thereby eliminating potential human error, and does not require users to find and use additional materials to use the safety device of the present disclosure. Further, since the IV solution name is printed on both sides of the tags, the tags provide dual-sided visibility, which further limits a health care professional's need to manipulate one of the tags to read the name of the IV solution. Seventh, since the adhesives and inks used in the safety device of the present disclosure are FDA approved (as further explained below), it is extremely unlikely that use of the safety device would contaminate the IV solution. Eighth, use of the safety device of the present disclosure is not time consuming because the user simply has to tear off one of the tags and remove the IV tubing line adhesive protective cover before attaching it to the IV tubing line. Ninth, the tags of the present disclosure are waterproof, which eliminates the potential for smeared ink.

Additional features and advantages are described herein, and will be apparent from, the following Detailed Description and the Figures.

BRIEF DESCRIPTION OF THE FIGURES

FIG. 1B is a back view of the IV bag/line safety device of FIG. 1A.

FIG. 2 is a cross-sectional view of the IV bag/line safety device of FIG. 1A taken substantially along line 2-2 of FIGS. 1A and 1B, wherein the thickness of each of the components of the IV bag/line safety device is enhanced for clarity.

FIG. 3D is a top perspective view of the IV bag of FIG. 3A.

FIG. 4 is cross-sectional view of the IV bag/line safety device of FIG. 1A taken substantially along line 2-2 of FIGS. 1A and 1B, and illustrates a hand of a bag preparer removing the bag attacher adhesive liner from the bag attacher adhesive disposed on and adhering to the head and the neck of the bag attacher, wherein the thickness of each of the components of the IV bag/line safety device is enhanced for clarity.

FIG. 6B is a top perspective view of the IV bag of FIG. 3A with the IV bag/line safety device of FIG. 1A attached thereto, and illustrates a hand of a user removing one of the tags from the tag set of the IV bag/line safety device, wherein the thickness of each of the components of the IV bag/line safety device is enhanced for clarity.

FIG. 7B is a cross-sectional view of the tag of FIG. 7A taken substantially along line 7B-7B of FIG. 7A, wherein the thickness of each of the components of the IV bag/line safety device is enhanced for clarity.

FIG. 7C is a cross-sectional view of the tag of FIG. 7A taken substantially along line 7B-7B of FIG. 7A, and illustrates a hand of a user: (a) removing the IV tubing line adhesive protective cover from the IV tubing line adhesive disposed on and adhering to the IV tubing line attacher, and (b) detaching the IV tubing line adhesive protective cover from the IV solution name displayer, wherein the thickness of each of the components of the IV bag/line safety device is enhanced for clarity.

FIG. 7D is a cross-sectional view of the tag of FIG. 7A taken substantially along line 7B-7B of FIG. 7A, and illustrates the tag after removal of the IV tubing line adhesive protective cover, wherein the thickness of each of the components of the IV bag/line safety device is enhanced for clarity.

FIG. 8A is a front view of the tag of FIG. 7D attached to an IV tubing line.

FIG. 8C is a cross-sectional view of the tag of FIG. 8A taken substantially along line 8C-8C of FIG. 8A, wherein the thickness of each of the components of the IV bag/line safety device is enhanced for clarity.

DETAILED DESCRIPTION

Intravenous Bag/Line Safety Device

Figure 1A:
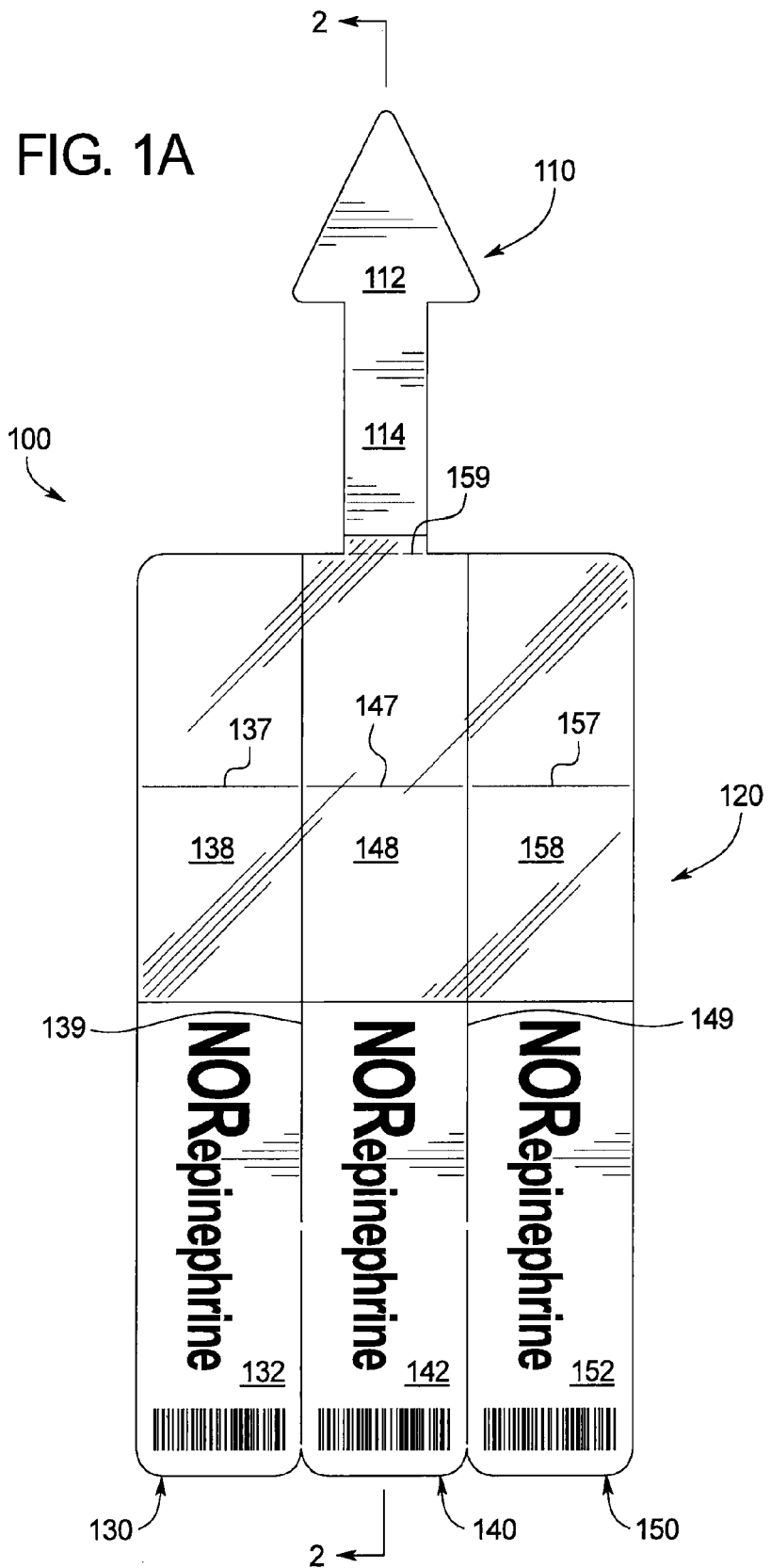
FIG. 1A is a front view of an IV bag/line safety device of one embodiment of the present disclosure.
Figure 3A:
FIG. 3A is a front view of an IV bag of one embodiment of the present disclosure.
Figure 3B:
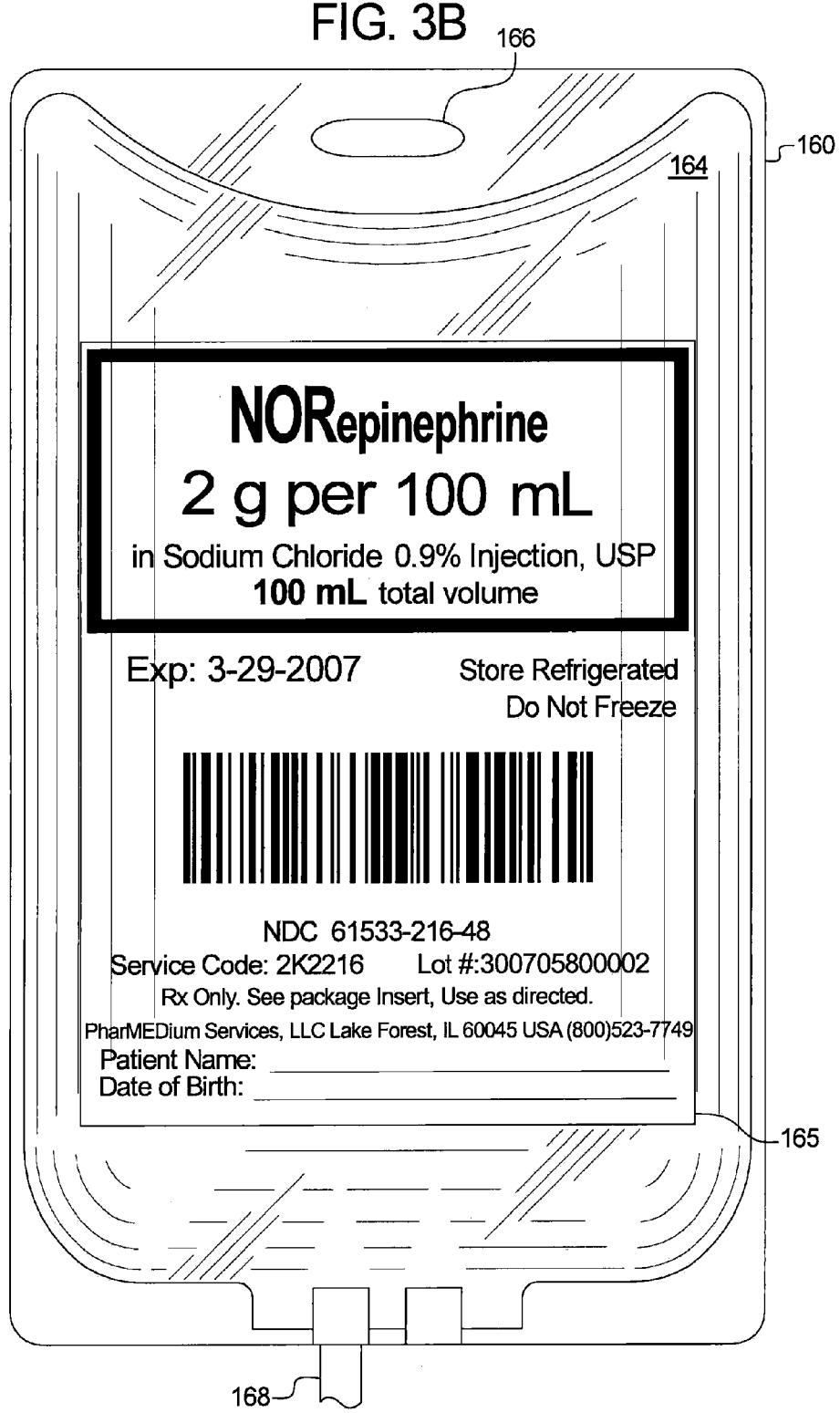
FIG. 3B is a back view of the IV bag of FIG. 3A.
Figure 3C:
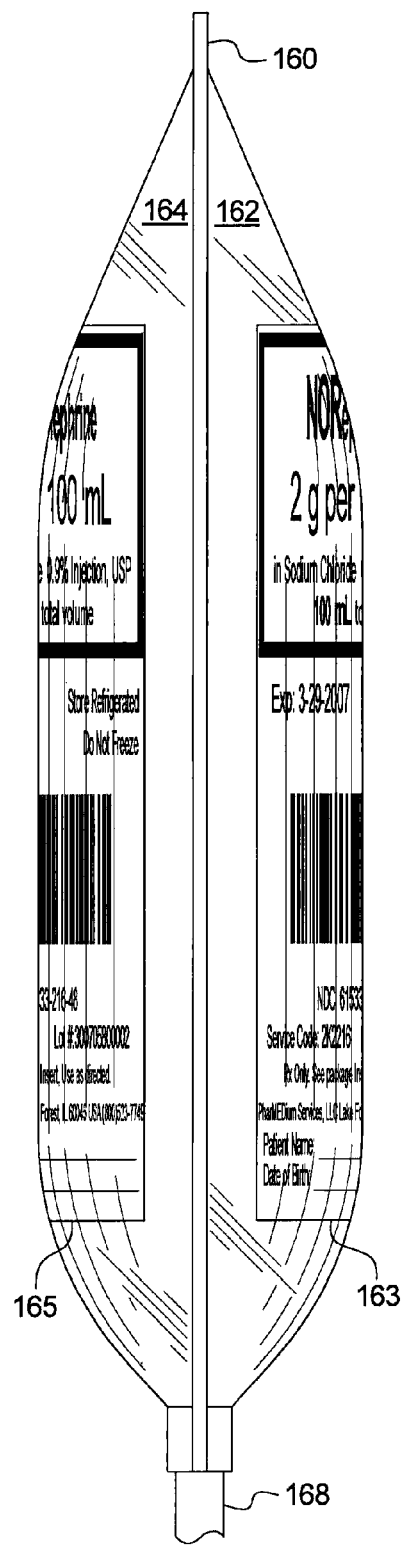
FIG. 3C is a side view of the IV bag of FIG. 3A.

In various embodiments, the IV bag/line safety device disclosed herein and, more specifically, the bag attacher, may be attached to an IV bag (and thus prepared for use) by any suitable bag preparer prior to delivery to a hospital or other medical facility. Typically, one or more manufacturers manufacture the IV bag and the IV tubing line. Subsequent to manufacturing, the IV bag and the IV tubing line are wrapped in one or more sealed outer bags and sterilized. After sterilization, the interior and the exterior of the IV bag and the interior and the exterior of the IV tubing line (which are contained within one or more outer bags) are sterile. After sterilization, the outer bag or bags (containing the IV bag and/or the IV tubing line) are delivered to an IV bag filler, such as a pharmacy or a pharmacy compounder (such as the assignee of this application). The IV bag filler fills the IV bag with an IV solution, i.e., with a liquid pharmaceutical and/or liquid nutrients suspended in a carrying liquid. It should be appreciated that, in certain instances, one IV bag filler fills the IV bag with a liquid pharmaceutical and/or liquid nutrients and another, different IV bag filler fills the IV bag with a carrying liquid. Before or after filling, an IV bag label attacher attaches one or more permanent labels to the IV bag identifying the solution (or the name of the pharmaceutical therein) contained by (or that will be contained by) the IV bag. After filling, the (filled) IV bag and the IV tubing line are wrapped in a sealed outer bag. It should be appreciated that after filling the interior of the IV bag remains sterile. The wrapped IV bag and tubing line are then delivered to a hospital or other medical facility. Upon receipt, a pharmacist (or other health care provider) catalogs the IV bag and stores it for future use by hospital staff, such as a health care provider in an ICU.

It should be appreciated that, in various embodiments, the IV bag/line safety device of the present disclosure may be attached to the IV bag at any suitable point during this process. That is, the IV bag/line safety device may be attached to the IV bag at any one of a variety of different times during the process and before a health care provider, such as a nurse working in an ICU, retrieves the IV bag for use with a patient. For example, in certain embodiments, the manufacturer of the IV bag attaches the IV bag/line safety device to the IV bag before sterilization. It should thus be appreciated that, in these embodiments, the IV bag/line safety device is sterilized along with the IV bag and/or the IV tubing line prior to delivery to an IV bag filler. In other embodiments, the IV bag filler attaches the IV bag/safety device to the IV bag after sterilization. That is, in these embodiments, upon receipt of the sterilized IV bag from the IV bag manufacturer, the IV bag filler removes the outer wrapping and attaches the IV bag/line safety device to the IV bag. It should be appreciated that, in these embodiments, the IV bag/line safety device is itself sterilized prior to being attached to the IV bag. In certain other embodiments, the IV bag/line safety device is attached to the IV bag by the pharmacist (or another health care provider) at the hospital or other medical facility after receipt from the IV bag filler. That is, in these embodiments, neither the IV bag manufacturer nor the IV bag filler attaches the IV bag/line safety device to the IV bag. It should also be appreciated that, in these embodiments, the IV bag/line safety device is itself sterilized prior to being attached to the IV bag.

To attach the safety device to the IV bag, prior to delivery to the hospital or other medical facility, a bag preparer: (a) removes the bag attacher adhesive liner from the bag attacher, thereby exposing the bag attacher adhesive; (b) inserts the head through the hanger hole of the IV bag; (c) folds the head over near the junction of the head and the neck; and (d) presses the head against the back surface of the IV bag and presses the neck against the front surface of the IV bag such that the bag attacher adhesive adheres to the front and back surfaces of the IV bag, thereby attaching the head, the neck, and, necessarily, the bag attacher and the safety device as a whole to the IV bag.

It should be appreciated from the above description that the IV bag is 'pre-prepared' with the IV bag/line safety device attached thereto when a health care provider (i.e., a user) desires to use that IV bag with a patient. FIGS. 1A to 9 and the descriptions below related thereto primarily focus on embodiments of the IV bag/line safety device in which: (a) a bag preparer prepares the IV bag/line safety device for use with an IV bag by attaching the IV bag/line safety device to the IV bag containing the appropriate IV solution before shipment to a hospital or medical care facility, and (b) a nurse working in an ICU uses the pre-prepared IV bag (with the IV bag/line safety device attached thereto) to administer the IV solution contained therein to a patient in the ICU and to identify an IV tubing line as containing that IV solution. It should be appreciated that these are only a few example embodiments of the present disclosure, and that the present disclosure is not limited to such use. For example, in certain other embodiments, the safety device is usable with one or more of a variety of different IV containers, such as syringes and IV manifolds.

Referring now to the Figures, FIGS. 1A, 1B, and 2 generally illustrate one example embodiment of IV bag/line safety device 100 of the present disclosure (which is sometimes referred to herein as 'safety device' for brevity). Safety device 100 includes a tag set 120 and a bag attacher 110 removably connected to tag set 120. Tag set 120 includes a first IV tubing line safety tag 130, a second IV tubing line safety tag 140, and a third IV tubing line safety tag 150, which are sometimes referred to herein as first tag 130, second tag 140, and third tag 150 for clarity and brevity. As best shown in FIGS. 1A and 1B, first tag 130 is removably connected to second tag 140 via a first perforated edge 139, third tag 150 is removably connected to second tag 140 via a second perforated edge 149, and second tag 140 is removably connected to bag attacher 110 via a third perforated edge 159. It should be appreciated that any one of the tags may be connected to the bag attacher via a perforated edge. For example, in one alternative embodiment, the first tag is removably connected to the bag attacher via a perforated edge.

As best shown in FIGS. 1A and 1B, first tag 130 includes a first first tag section or a first IV solution name displayer 132 removably connected to a second first tag section or a first IV tubing line adhesive protective cover 134 via a first tag perforated edge 137, second tag 140 includes a first second tag section or a second IV solution name displayer 142 removably connected to a second second tag section or a second IV tubing line adhesive protective cover 144 via a second tag perforated edge 147, and third tag 150 includes a first third tag section or a third IV solution name displayer 152 removably connected to a second third tag section or a third IV tubing line adhesive protective cover 154 via a third tag perforated edge 157. A name of an IV solution or the pharmaceutical included or contained therein, which in this example is norepinephrine, is printed on the front surface (as illustrated in FIG. 1A) and also on the back surface (as illustrated in FIG. 1B) of each of first IV solution name displayer 132, second IV solution name displayer 142, and third IV solution name displayer 152. A barcode is also included on each IV solution name displayer. The barcode, when read by a barcode reader, provides certain information about the IV solution, such as (but not limited to) the IV solution name, the concentration of the pharmaceutical therein, dosage information of the pharmaceutical therein, and pharmaceutical class of the pharmaceutical therein. It should be appreciated that, in various embodiments: (a) the barcode may be located in any suitable area of the tags or the safety device; (b) fewer than all of the tags include a barcode; (c) none of the tags include a barcode; and (d) the barcode may represent any suitable data or information. It should be appreciated that, in certain embodiments, the safety device does not include a bar code.

As best illustrated in FIG. 2, second tag 140 includes a second tag laminate section or a second IV tubing line attacher 148 having a second IV tubing line adhesive 146 disposed on and adhering to its back surface (i.e., the surface of second IV tubing line attacher 148 opposite the surface of second IV tubing line attacher 148 shown in FIG. 1A). In this example, second IV tubing line adhesive 146 is disposed on all or substantially all of the back surface of second IV tubing line attacher 148. As best illustrated in FIGS. 1A, 1B, and 2, a portion of the front surface of second IV solution name displayer 142 is attached to second IV tubing line attacher 148 via second IV tubing line adhesive 146, and all or substantially all of the front surface of second IV tubing line adhesive protective cover 144 is removably attached to second IV tubing line attacher 148 via second IV tubing line adhesive 146. The surface of second IV tubing line adhesive protective cover 144 that is removably attached to second IV tubing line attacher 148 via second IV tubing line adhesive 146 is coated or lined with a release coating that enables a user to quickly and easily peel second IV tubing line adhesive protective cover 144 off of second IV tubing line attacher 148 (as described in detail below). More particularly, the release coating controls adhesion and predisposes second IV tubing line adhesive protective cover 144 to separate from second IV tubing line adhesive 146. The release coating also reduces stress on second IV tubing line attacher 148 and prevents second IV tubing line attacher 148 from curling during the removal of second IV tubing line adhesive protective cover 144. Additionally, in this illustrated embodiment, a portion of the front surface of neck 114 of bag attacher 110 (described below) is removably attached to second IV tubing line attacher 148 via second IV tubing line adhesive 146, though it should be appreciated that in other embodiments there is no such attachment.

Similarly, first tag 130 includes a first tag laminate section or a first IV tubing line attacher 138 having a first IV tubing line adhesive (not shown) disposed on and adhering to its back surface (i.e., the surface of first IV tubing line attacher 138 opposite the surface of first IV tubing line attacher 138 shown in FIG. 1A). In this example, the first IV tubing line adhesive is disposed on all or substantially all of the back surface of first IV tubing line attacher 138. As best illustrated in FIGS. 1A and 1B, a portion of the front surface of first IV solution name displayer 132 is attached to first IV tubing line attacher 138 via the first IV tubing line adhesive, and all or substantially all of the front surface of first IV tubing line adhesive protective cover 134 is removably attached to first IV tubing line attacher 138 via the first IV tubing line adhesive. The surface of first IV tubing line adhesive protective cover 134 that is removably attached to first IV tubing line attacher 138 via the first IV tubing line adhesive is coated or lined with a release coating (as explained above) that enables a user to quickly and easily peel first IV tubing line adhesive protective cover 134 off of first IV tubing line attacher 138 (as described in detail below).

Similarly, third tag 150 includes a third tag laminate section or a third IV tubing line attacher 158 having a third IV tubing line adhesive (not shown) disposed on and adhering to its back surface (i.e., the surface of third IV tubing line attacher 158 opposite the surface of third IV tubing line attacher 158 shown in FIG. 1A). In this example, the third IV tubing line adhesive is disposed on all or substantially all of the back surface of third IV tubing line attacher 158. As best illustrated in FIGS. 1A and 1B, a portion of the front surface of third IV solution name displayer 152 is attached to third IV tubing line attacher 158 via the third IV tubing line adhesive, and all or substantially all of the front surface of third IV tubing line adhesive protective cover 154 is removably attached to third IV tubing line attacher 158 via the third IV tubing line adhesive. The surface of third IV tubing line adhesive protective cover 154 that is removably attached to third IV tubing line attacher 158 via the third IV tubing line adhesive is coated or lined with a release coating (as explained above) that enables a user to quickly and easily peel third IV tubing line adhesive protective cover 154 off of third IV tubing line attacher 158 (as described in detail below).

In this example, first IV solution name displayer 132, second IV solution name displayer 142, and third IV solution name displayer 152 are made from a white, rigid polyester that has a designated amount of rigidity. The IV solution name or the name of the pharmaceutical included therein is printed on the rigid polyester in black UV Flexo ink. This designated amount of rigidity enables each of the first IV solution name displayer, the second IV solution name displayer, and the third IV solution name displayer to, after attachment to an IV tubing line (as explained in detail below), retain its shape and its orientation in relation to the IV tubing line. This, along with the fact that black text is used on a white background, enables a user (such as a nurse) to easily read the name of the IV solution in any lighting conditions (such as the dim lighting conditions in an ICU). Also, in this example, first IV tubing line attacher 138, second IV tubing line attacher 148, third IV tubing line attacher 158, the first IV tubing line adhesive, second IV tubing line adhesive 146, and the third IV tubing line adhesive are transparent or substantially transparent. This enables the user to, after attachment to an IV tubing line (as explained in detail below), see through the IV tubing line attacher and the IV tubing line adhesive and view the IV solution flowing through the section of the IV tubing line to which the IV tubing line attacher and IV tubing line adhesive is attached. It should be appreciated, however, that in certain other embodiments, one or more of the first IV tubing line attacher, the second IV tubing line attacher, the third IV tubing line attacher, the first IV tubing line adhesive, the second IV tubing line adhesive, and the third IV tubing line adhesive are translucent or opaque.

It should be appreciated that the first IV tubing line adhesive protective cover is removably attached to the first IV tubing line adhesive, the second IV tubing line adhesive protective cover is removably attached to the second IV tubing line adhesive and the neck, and the third IV tubing line adhesive protective cover is removably attached to the third IV tubing line adhesive such that when one of those IV tubing line adhesive protective covers (and/or the neck) is removed from its corresponding IV tubing line adhesive, all or substantially all of that IV tubing line adhesive remains disposed on and adhering to the back surface of the corresponding IV tubing line attacher. That is, the release coating on the IV tubing line protective covers ensure that when a user removes one of those IV tubing line adhesive protective covers (and/or the neck) to attach the corresponding IV solution name displayer and IV tubing line attacher to an IV tubing line, such as by peeling that IV tubing line adhesive protective cover off of the IV tubing line adhesive (as described in detail below), the corresponding IV tubing line adhesive does not stick to that removed IV tubing line adhesive protective cover. It should also be appreciated that the IV solution name displayers, the IV tubing line adhesive protective covers, and the neck do not interfere with the adhesive properties of the IV tubing line adhesives to which they are removably attached. More specifically, the IV solution name displayers, the IV tubing line adhesive protective covers, and the neck do not affect the ability of the IV tubing line adhesives to which they are removably attached to adhere the tags to the IV tubing line.

Although the example embodiment of the safety device described above with respect to FIGS. 1A, 1B, and 2 (and below with respect to FIGS. 3A to 8C) includes three tags, it should be appreciated that in other embodiments the safety device may include any suitable quantity of tags, such as (but not limited to) one tag, two tags, four tags, or five tags. It should also be appreciated that, in other embodiments, one or more tags each include an IV solution name printed on only one of their surfaces rather than both of their surfaces. It should further be appreciated that, in various embodiments, one or more tags include other information about an IV solution, such as (but not limited to) IV solution concentration, IV solution dosage information, IV solution class, and/or any other suitable feature of the IV solution printed on one or more of its surfaces. For example, in one embodiment, two of the tags each include an IV solution name printed on one or more of their surfaces and one of the tags includes an IV solution concentration printed on one or more of its surfaces. In certain embodiments, each of the tags includes an RFID configured to identify that tag and/or the IV solution printed on that tag. In some embodiments, the tags have a color other than white. These colors may be associated with certain information, such as a particular pharmaceutical, class of pharmaceuticals, or pharmaceutical concentration. In one embodiment, the tags are colored black and the IV solution name is printed in white ink. In various other embodiments, inks of a color other than black or white may be employed.

Bag attacher 110 includes a triangular head 112, a rectangular neck 114 connected at one end to head 112, a bag attacher adhesive 116 disposed on and adhering to one surface of head 112 and neck 114, and a bag attacher adhesive protective liner 118 (referred to herein as 'bag attacher adhesive liner') removably attached to and covering bag attacher adhesive 116. It should be appreciated that head 112 may be any other suitable shape (such as a ring). It should also be appreciated that the head and the neck may be of any suitable size or dimensions. In this example, bag attacher adhesive 116 is disposed on and adheres to the majority of the back surface of head 112 and neck 114 (i.e., the surfaces of head 112 and neck 114 opposite the surfaces of head 112 and neck 114 shown in FIG. 1A). More specifically, in this embodiment bag attacher adhesive 116 is disposed on and adheres to substantially all of the back surface of head 112 and the majority the back surface of neck 114. As best shown in FIG. 2, in this example a relatively small area of neck 114 adjacent to tag set 120 does not include bag attacher adhesive 116. As best illustrated in FIGS. 1B and 2, since bag attacher adhesive 116 is disposed on and adheres to substantially all of the back surface of head 112 and the majority of the back surface of neck 114, bag attacher adhesive liner 118 covers substantially all of the back surface of head 112 and the majority of the back surface of neck 114.

It should be appreciated that the bag attacher adhesive liner is removably attached to the bag attacher adhesive such that when the bag attacher adhesive liner is removed, all or substantially all of the bag attacher adhesive remains disposed on and adhering to the back surface of the bag attacher. That is, the bag attacher adhesive liner is a releasable liner that does not compromise or permanently bond to the bag attacher adhesive. Thus, when a bag preparer removes the bag attacher adhesive liner to attach the bag attacher to an IV bag, such as by peeling off the bag attacher adhesive liner (as described in detail below), the bag attacher adhesive does not stick to the bag attacher adhesive liner.

It should be appreciated that certain of the Figures, including at least FIGS. 2, 4, 5C, 5D, 6A, 7B, 7C, 7D, 8B, and 8C, enhance the thickness and certain other dimensions of certain components of the safety device for clarity. It should be appreciated that, in one example embodiment: (a) the head is approximately 1.1 in. long, 1.25 in. wide, and 7 milliinches thick; (b) the neck is approximately 1.5 in. long, 0.5 in. wide, and 7 milliinches thick; (c) each of the first IV solution name displayer, the second IV solution name displayer, and the third IV solution name displayer is approximately 3 in. long, 1 in. wide, and 7 milliinches thick; (d) each of the first IV tubing line adhesive protective cover, the second IV tubing line adhesive protective cover, and the third IV tubing line adhesive protective cover is approximately 1.294 in. long, 1 in. wide, and 7 milliinches thick; (e) each of the first IV tubing line attacher, the second IV tubing line attacher, and the third IV tubing line attacher is approximately 2.1 in. long, 1 in. wide, and 2.2 milliinches thick; (f) the first IV tubing line adhesive, the second IV tubing line adhesive, and the third IV tubing line adhesive are approximately 1 milliinch thick; and (g) the bag attacher adhesive is approximately 1 milliinch thick. It should be appreciated that these dimensions reflect one example embodiment of the safety device, and that the safety device may have any suitable dimensions.

Bag attacher 110 is configured to attach safety device 100 to an IV bag containing the IV solution including the pharmaceutical that is printed on the front and back surfaces of first IV solution name displayer 132, second IV solution name displayer 142, and third IV solution name displayer 152, which is the pharmaceutical norepinephrine in this example. FIGS. 3A, 3B, 3C, and 3D illustrate a front view, a back view, a side view, and a perspective view of an example IV bag 160 containing an IV solution including norepinephrine. IV bag 160 includes a front surface 162, an opposing back surface 164, and an oval-shaped hanger opening 166 punched through the top of IV bag 160. It should be appreciated that the IV bag may employ a hanger opening of any suitable shape and size. A front permanent label 163 is affixed to front surface 162 and a back permanent label 165 is affixed to back surface 164. Front permanent label 163 and back permanent label 165 include a variety of information regarding the IV solution contained in IV bag 160. For example, in various embodiments, front permanent label 163 and/or back permanent label 165 include one or more of: (a) the name of the IV solution or the pharmaceutical included therein, (b) the concentration of the IV solution or the pharmaceutical included therein, (c) the total amount of the IV solution in the IV bag, (d) the expiration date of the IV solution, (d) the lot number of the IV solution, (f) one or more instructions for administering and/or storing the IV solution, and (g) a bar code used to identify the IV bag, the IV solution, or the pharmaceutical included therein. IV bag 160 is connected to an IV tubing line 168, through which the IV solution contained in IV bag 160 flows from IV bag 160 into a patient (not shown).

It should be appreciated that IV bag 160 is one of a variety of different types of IV bags in one of a plurality of different sizes. It should also be appreciated that any suitable type of IV bag in any suitable size may be used with the safety device of the present disclosure. It should further be appreciated that the safety device of the present disclosure may be used in conjunction with an IV bag containing any suitable IV solution in liquid form. In some embodiments, the IV bag includes information printed on the bag itself instead of, or in addition to, any permanent labels on the IV bag. In some embodiments, the IV bag includes a permanent label on only the front surface or the back surface. It should be appreciated that the IV bag may include any suitable quantity or configuration of permanent labels.

As noted above, the bag attacher of the safety device is configured to attach the safety device to an IV bag containing the IV solution printed on the first IV solution name displayer, the second IV solution name displayer, and the third IV solution name displayer. As also explained above, a bag preparer, such as the IV bag filler or manufacturer, attaches the safety device to the IV bag before shipment to the hospital or other medical care facility. This ensures that the safety device is ready for use whenever a nurse (or any other suitable user) working in an ICU (or any other suitable medical facility) receives and desires to use the IV bag (with the safety device attached thereto).

To attach the safety device to the IV bag, the bag preparer: (a) removes the bag attacher adhesive liner from the head and the neck, thereby exposing the bag attacher adhesive; (b) inserts the head through the hanger hole of the IV bag; (c) folds the head over near the junction of the head and the neck; and (d) presses the head against the back surface of the IV bag and presses the neck against the front surface of the IV bag such that the bag attacher adhesive adheres to the front and back surfaces of the IV bag, thereby attaching the head; the neck; and, necessarily, the bag attacher and the safety device as a whole to the IV bag. After attachment, the safety device provides visual cues to the user that invite the user to detach the tags (or the entire tag set) from the connected safety device. After detaching one or more of the tags, the user may attach those tags to an IV tubing line connected to the IV bag through which the IV solution contained in the IV bag flows from the IV bag into a patient. Since the name of the IV solution printed on the tags is the IV solution contained in the IV bag to which the safety device is attached, the tags identify the IV tubing line to which they are attached as containing the IV solution in the IV bag. This enables the user to quickly and easily identify which IV solution a given IV tubing line (having one of more of the tags attached thereto) contains. This is particularly useful when multiple IV solutions are being administered to a patient via multiple IV bags and multiple IV tubing lines. If each of the IV tubing lines includes one or more of the tags, the user may use the tags to quickly and easily differentiate which of the IV tubing lines contains which IV solution.

As illustrated in FIG. 4, in preparation for attachment to IV bag 160, a bag preparer 190 removes bag attacher adhesive liner 118 by peeling bag attacher adhesive liner 118 off of, or otherwise removing it from, bag attacher adhesive 116. This exposes bag attacher adhesive 116, which is disposed on and adheres to the back surface of bag attacher 110. To attach bag attacher 110 to IV bag 160 using bag attacher adhesive 116, bag preparer 190: (a) inserts head 112 through hanger hole 166, (b) folds head 112 down near the junction of head 112 and neck 114, and (c) applies a suitable force to the front surface of head 112 against back surface 164 of IV bag 160 such that bag attacher adhesive 116 disposed on and adhering to the back surface of head 112 adheres to back surface 164 of IV bag 160, thereby attaching head 112 to back surface 164 (not shown). Similarly, after inserting head 112 through hanger hole 166, bag preparer 190 applies a suitable force to the front surface of neck 114 against front surface 160 of IV bag 160 such that bag attacher adhesive 116 disposed on and adhering to the back surface of neck 114 adheres to front surface 162 of IV bag 160, thereby attaching neck 114 to front surface 162 (not shown).

Once the head and the neck are attached to the front and the back surfaces of the IV bag, respectively, it should be appreciated that none of the bag attacher adhesive leaches into the IV bag and none of the ink printed on any components of the safety device bleeds or smears. That is, the IV solution contained in the IV bag is not contaminated by the safety device or any components thereof when the safety device is attached to the IV bag. It should also be appreciated that no or a small amount of extra bag attacher adhesive is exposed once the bag attacher is attached to the IV bag.

In some embodiments, the surfaces of the IV bag to which the head and the neck attach may be switched. That is, the bag preparer may attach the safety device to the IV bag by attaching the head to the front surface of the IV bag and the neck to the back surface of the IV bag.

In various embodiments, the bag attacher does not utilize the head passing through the hanger hole to attach the safety device to the IV bag. Rather, in these embodiments, to attach the safety device to the IV bag in this embodiment, the bag preparer: (a) removes the bag attacher adhesive liner from the bag attacher, thereby exposing the bag attacher adhesive; and (b) presses the bag attacher against the front or back surface of the IV bag such that the bag attacher adhesive adheres to that surface and, therefore, attaches the bag attacher and, necessarily, the safety device as a whole to the IV bag.

In another embodiment, the bag attacher does not include any bag attacher adhesive or a bag attacher adhesive liner. In this embodiment, the head is shaped and sized such that once the head passes through the hanger hole of the IV bag, the head will not return back through the hanger hole without substantial manipulation by the bag preparer (or the user). Thus, to attach the safety device to the IV bag in this embodiment, the bag preparer manipulates the head and passes the head through the hanger hole. Once it passes through the hanger hole, the head returns to substantially its original shape and size, thereby preventing the head from returning back through the hanger hole and, therefore, preventing the safety device from falling off of the IV bag (without bag preparer or user manipulation). In certain embodiments the bag attacher adhesive is disposed on one surface of the head and not on the neck. In other embodiments, the bag adhesive is disposed on one surface of the neck and not the head.

FIGS. 5A, 5B, 5C, and 5D illustrate a front view, a back view, a side view, and a perspective view of IV bag 160 with safety device 100 attached thereto. It should be appreciated from these Figures that the safety device is attached to the IV bag in addition to the front permanent label, the back permanent label, and any printing on the IV bag itself (not shown). It should also be appreciated from these Figures that no portion of the tag set adheres to or is attached to the IV bag while the safety device is attached to the IV bag. Rather, it is the bag attacher, not the tag set, that is adhered to the IV bag. It should further be appreciated from these Figures that the head and the neck are sized such that they do not interfere with, obstruct, or destroy any part of the front permanent label, the back permanent label, or any printing on the bag (not shown) after the head and the neck are attached to the IV bag via the bag attacher adhesive. That is, when attached to the IV bag, the head and the neck are sized such that they do not overlap or destroy any of the printing included on the front permanent label, the back permanent label, or the IV bag itself (not shown).

These features of the safety device highlight certain of the benefits of its use with an IV bag. Since the safety device is employed in addition to any permanent labels on an IV bag rather than being a removable section of a permanent label on the IV bag, there is little chance that use of the safety device would result in a part of that permanent label being destroyed because the safety device and the permanent label do not physically interact. Thus, the safety device of the present disclosure significantly reduces the possibility that vital information could be accidently removed from the permanent label or rendered illegible through the use of the safety device. This provides peace of mind to health care providers and reassures them that use of the safety device will not negatively impact the use of existing IV bag permanent labels, and can be safety used as an addition to existing IV bag permanent labels without interference. Additionally, since the safety device of the present disclosure and, necessarily, the tags, are attached to the IV bag, the safety device provides a high level of convenience to users because the tags, the IV bag, and the IV tubing line to which the tags are attached are all in one place. In other words, the user does not, for example, have to visit different areas of an operating room or a prep room to find the IV bags and the tags. This reduces the number of steps and materials required to prepare the IV bag and the safety device, thereby reducing overall prep time.

Figure 5A:
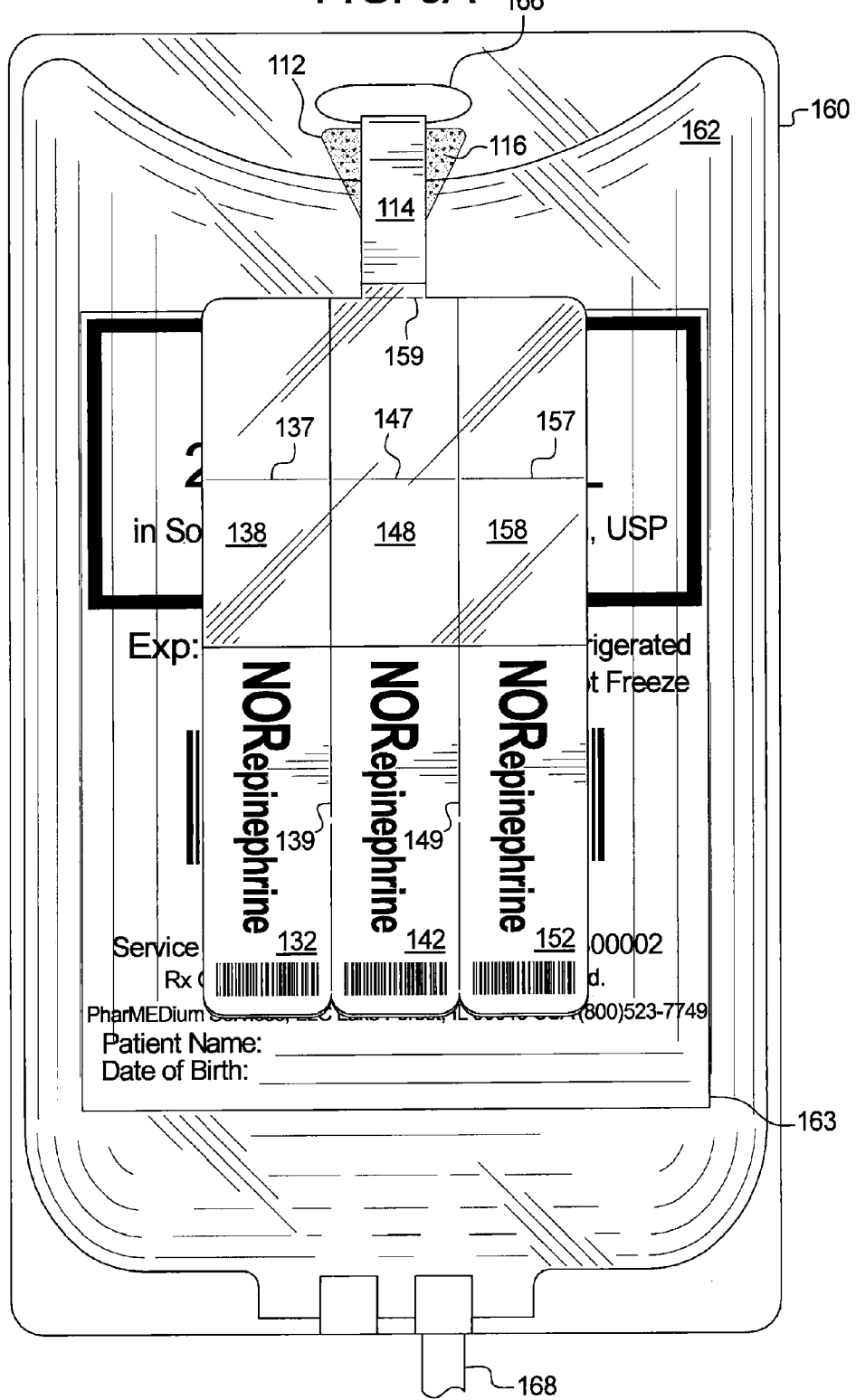
FIG. 5A is a front view the IV bag of FIG. 3A with the IV bag/line safety device of FIG. 1A attached thereto.
Figure 5B:
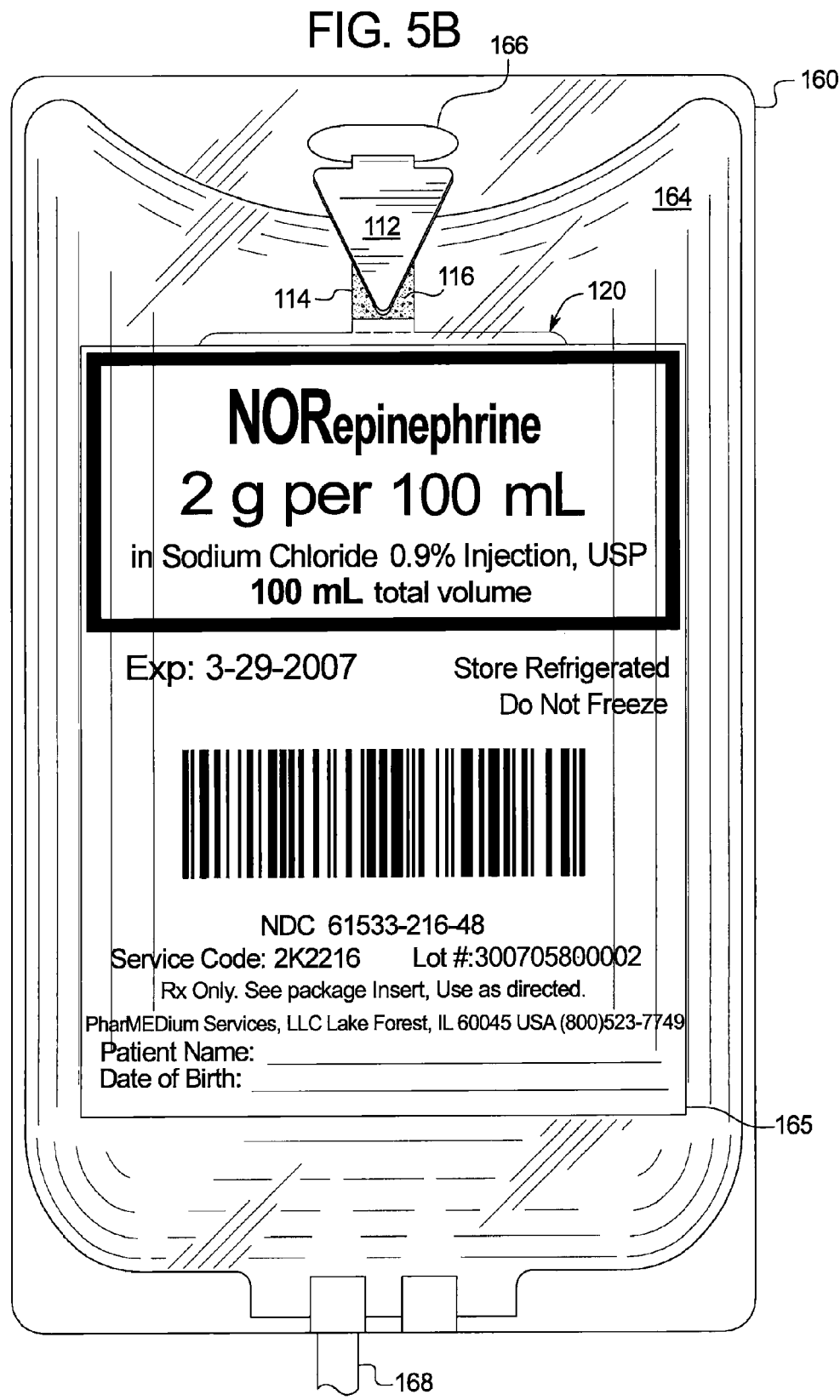
FIG. 5B is a back view of the IV bag of FIG. 3A with the IV bag/line safety device of FIG. 1A attached thereto.

As shown in FIGS. 5A and 5B, tag set 120 may obstruct certain portions of front permanent label 163 immediately after attachment. It should be appreciated, however, that since: (a) no portion of the tag set is attached to the IV bag, and (b) the neck is sized such that it does not interfere with, obstruct, or destroy any portions of the front permanent label, once the tag set is detached from bag attacher by a user (as described further below) the front permanent label will no longer be obstructed.

Figure 5C:
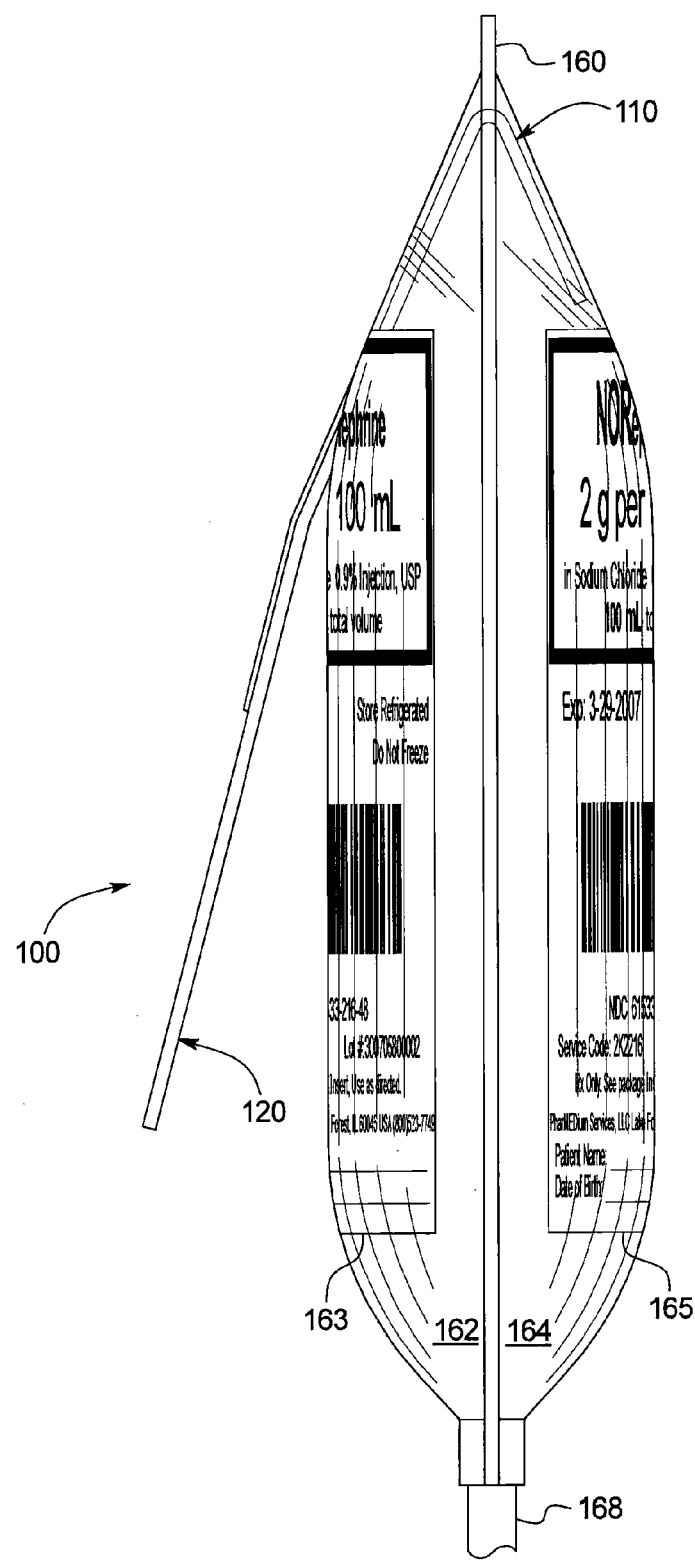
FIG. 5C is a side view of the IV bag of FIG. 3A with the IV bag/line safety device of FIG. 1A attached thereto, wherein the thickness of each of the components of the IV bag/line safety device is enhanced for clarity.
Figure 5D:
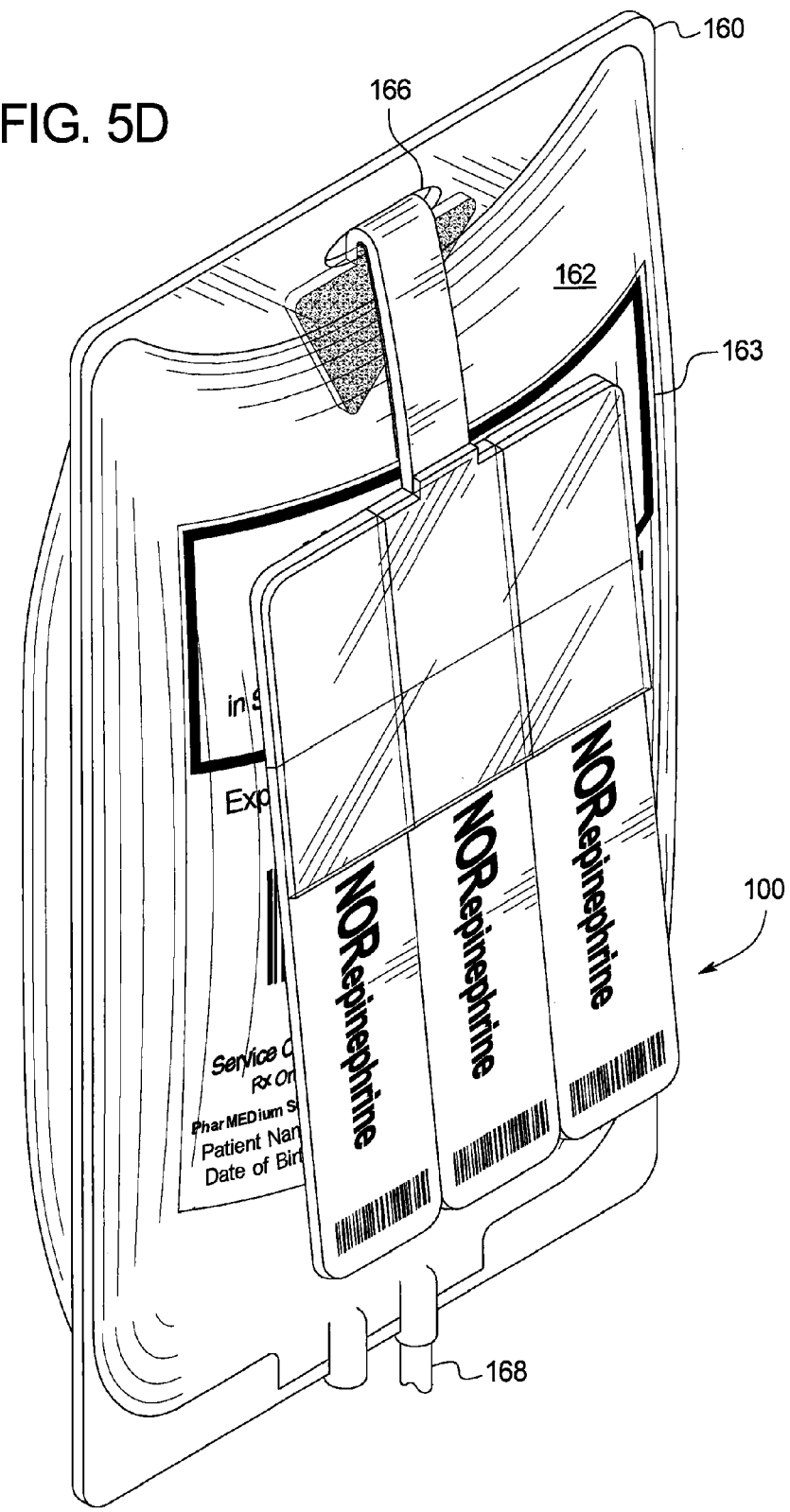
FIG. 5D is a top perspective view of the IV bag of FIG. 3A with the IV bag/line safety device of FIG. 1A attached thereto, wherein the thickness of each of the components of the IV bag/line safety device is enhanced for clarity.

After attachment to the IV bag, the safety device provides visual cues to a user, such as a nurse working in an ICU, that invite the user to detach the tag set, as a whole, from the bag attacher, or to detach one or more of the first tag, the second tag, and the third tag from the tag set (i.e., from one or more of the other tags of the tag set). As best illustrated in FIGS. 5C and 5D, since safety device 100 is attached to IV bag 160 via bag attacher adhesive 116 disposed on head 112 and neck 114, tag set 120 hangs or dangles off of IV bag 160 from below the attachment point of neck 114 to IV bag 160, similar to the way in which a price tag hangs off of a piece of clothing. The fact that the tag set itself is not attached to, and is loosely hanging or dangling from, the IV bag over the permanent label (and not as part of the permanent label) cues the user to detach the tag set as a whole from the bag attacher or to detach one or more of the tags (similar to how one would detach a price tag from a recently-purchased item of clothing before using the clothing). Upon viewing the dangling tags, the nurse (or other user) will intuitively want to remove them; that is, the hanging or dangling tags clearly convey to the nurse that they are removable and should be removed. When the safety device of various embodiments of the present disclosure is initially attached to the IV bag, the tag set may block all or a portion of one of the permanent labels on the IV bag. The fact that the user may not be able to read all or part of that permanent label also cues the user to detach the tag set from the bag attacher. In other words, the use of the safety device in some ways requires the user to remove the tags to properly read the permanent label on the IV bag.

As explained above, in this example the bag preparer attaches the safety device to the IV bag prior to delivery to the hospital or other medical facility. In certain other embodiments, the bag preparer and the user are the same. In one of these embodiments, the user attaches the safety device to the IV bag immediately prior to administering the IV solution contained in that IV bag to a patient. In another one of these embodiments, the user attaches the safety device to the IV bag upon receipt of the safety device and the IV bag from the manufacturer. In other words, in this embodiment the user attaches the safety device to the IV bag to prepare them use at a subsequent point in time (e.g., later that day or later that week).

As best illustrated in FIGS. 1A and 2, a user (e.g., a nurse working in an ICU) may disconnect tag set 120 from bag attacher 110 by tearing or pulling tag set 120 off of bag attacher 110 along third perforated edge 159. Additionally, since a portion of the front surface of neck 114 is removably attached to second IV tubing line adhesive 146, the user also peels neck 114 off of, or otherwise removes neck 114 from, second IV tubing line adhesive 146 to disconnect tag set 120 from bag attacher 110. After disconnecting tag set 120 from bag attacher 110, the user may disconnect first tag 130, second tag 140, and third tag 150 from one another by tearing or pulling first tag 130 off of second tag 140 along first perforated edge 139, and tearing or pulling third tag 150 off of second tag 140 along second perforated edge 149.

Figure 6A:
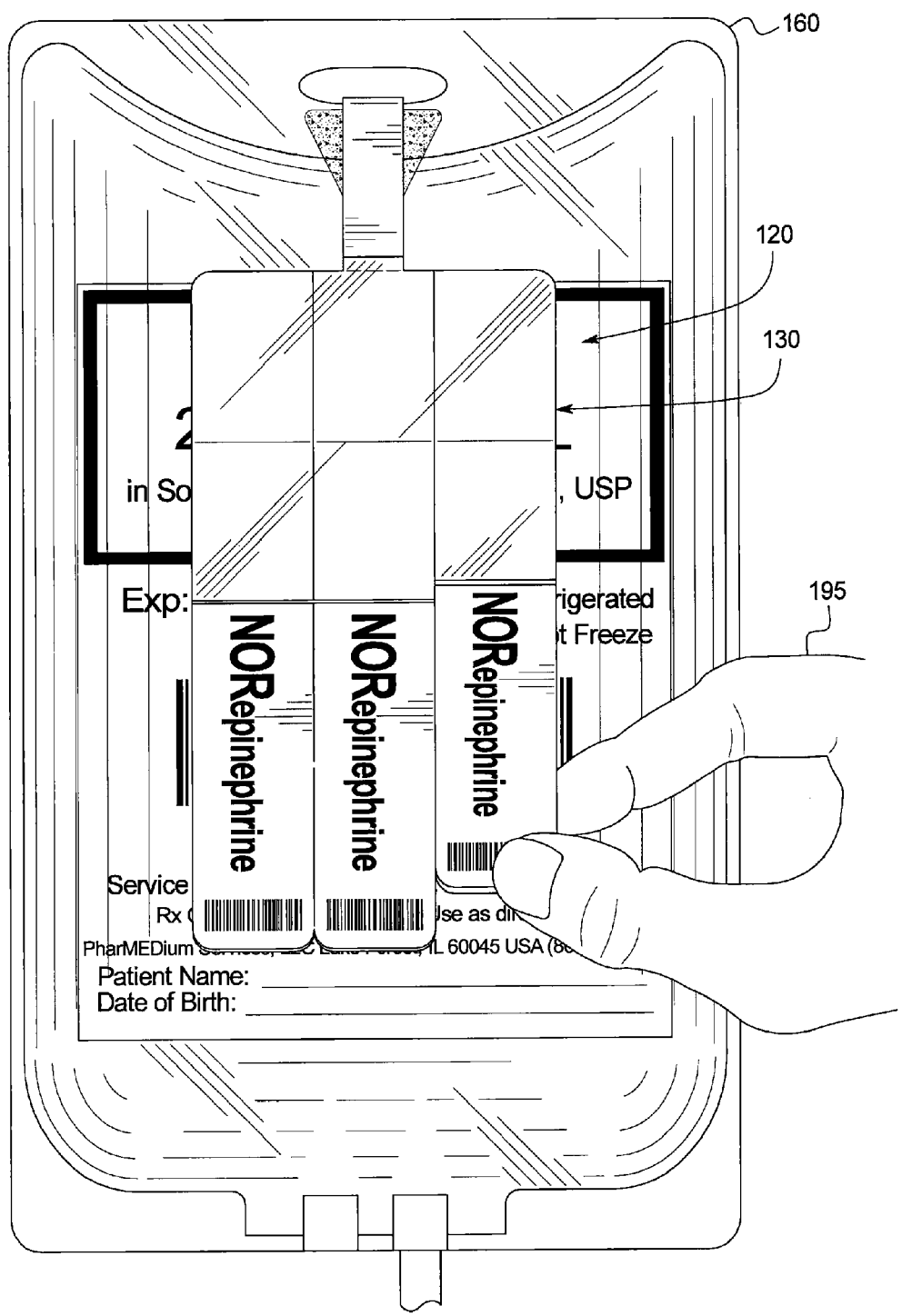
FIG. 6A is a front view of the IV bag of FIG. 3A with the IV bag/line safety device of FIG. 1A attached thereto, and illustrates a hand of a user removing one of the tags from the tag set of the IV bag/line safety device.

Rather than disconnecting tag set 120 from bag attacher 110 and then disconnecting first tag 130, second tag 140, and third tag 150 from one another, the user may individually disconnect first tag 130 and/or third tag 150 from second tag 140 (i.e., from tag set 120) while second tag 140 (and, necessarily, tag set 120) is still removably connected to bag attacher 110. More specifically, the user may disconnect first tag 130 from tag set 120 by tearing or pulling first tag 130 off of second tag 140 along first perforated edge 139. Similarly, the user may disconnect third tag 150 from tag set 120 by tearing or pulling third tag 150 off of second tag 140 along second perforated edge 149. For example, FIGS. 6A and 6B illustrate user 195 disconnecting third tag 150 from tag set 120 by tearing or pulling third tag 150 off of second tag 140 along second perforated edge 149.

Figure 7A:
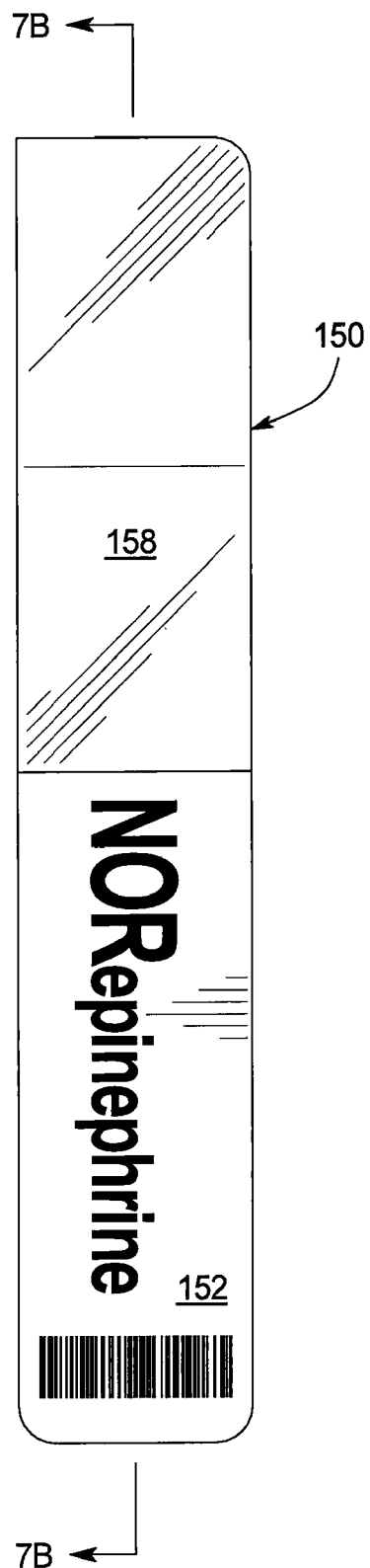
FIG. 7A is a front view of one of the tags removed from the tag set of the IV bag/line safety device.

After one or more of the first tag, the second tag, and the third tag are disconnected from the bag attacher and each of the other tags, the user may attach those tags to the IV tubing line of the IV bag to identify, via the printed IV solution name on each side of the tags, the IV solution contained in the IV bag connected to that IV tubing line. FIGS. 7A, 7B, 7C, and 7D illustrate a hand of a user 195 preparing third tag 150 for attachment to IV tubing line 168. As best illustrated in FIGS. 7C and 7D, to prepare third tag 150 for attachment to IV tubing line 168, the hand of user 195 removes third IV tubing line adhesive protective cover 154 from third tag 150 by: (a) peeling third IV tubing line adhesive protective cover 154 off of, or otherwise removing third IV tubing line adhesive protective cover 154 from, third IV tubing line adhesive 156, thereby exposing third IV tubing line adhesive 156; and (b) disconnecting third IV tubing line adhesive protective cover 154 from third IV solution name displayer 152 by tearing or pulling third IV tubing line adhesive protective cover 154 off of third IV solution name displayer 152 along third tag perforated edge 157.

After exposing third IV tubing line adhesive 156, the user attaches third tag 150 to IV tubing line 168 using third IV tubing line adhesive 156. Specifically, the user attaches third tag 150 to IV tubing line 168 by: (a) wrapping the portion of third IV tubing line attacher 158 having exposed third IV tubing line adhesive 156 around IV tubing line 168 while applying a suitable force to the front surface of third IV tubing line attacher 158 against IV tubing line 168 such that third IV tubing line adhesive 156 disposed on and adhering to the back surface of third IV tubing line attacher 158 adheres to the outer surface of IV tubing line 168, and (b) applying a suitable force to the front surface of third IV tubing line attacher 158 against the back surface of third IV solution name displayer 152 such that third IV tubing line adhesive 156 disposed on and adhering to the back surface of third IV tubing line attacher 158 adheres to the back surface of third IV solution name displayer 152.

Figure 8B:
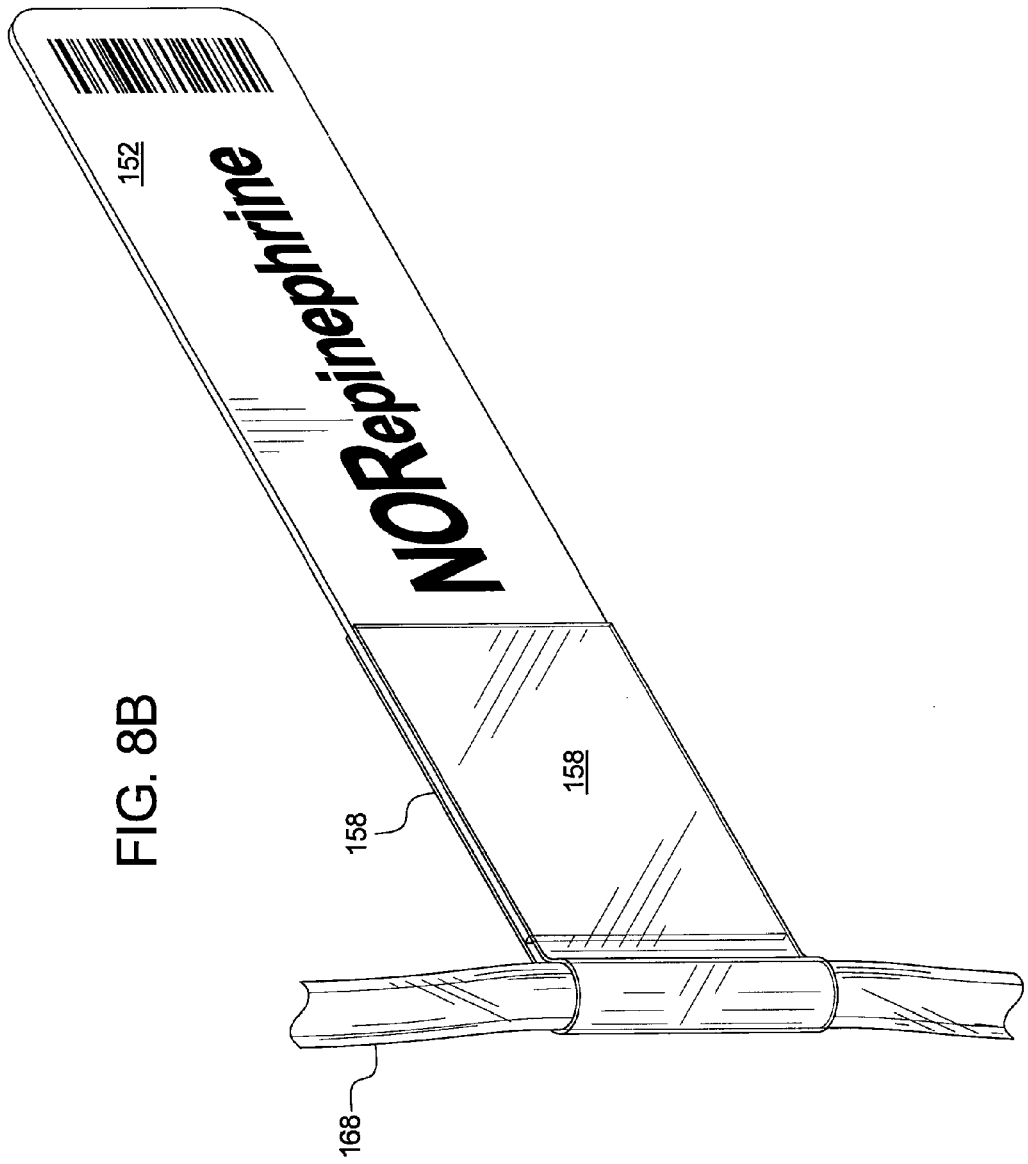
FIG. 8B is a top perspective view of the tag of FIG. 7D attached to the IV tubing line, wherein the thickness of each of the components of the IV bag/line safety device is enhanced for clarity.

FIGS. 8A, 8B, and 8C illustrate third tag 150 attached to IV tubing line 168. As best illustrated in FIG. 8B, third tag 150 has a designated amount of rigidity such that it maintains its shape and orientation (substantially perpendicular to IV tubing line 168) after it is attached to IV tubing line 168. Additionally, as best illustrated in FIGS. 8A and 8B, since third IV tubing line attacher 158 and third IV tubing line adhesive 156 are transparent or substantially transparent, the user is able to view the liquid IV solution flowing through IV tubing line 168.

These features emphasize the ease of use, convenience, and safety benefits of the safety device of the present disclosure. The designated amount of rigidity of the tags enables a user to readily view the full IV solution name (or the name of the pharmaceutical included therein) printed on the tag when it is attached to the IV tubing line without having to significantly handle or manipulate the tag, if any handling or manipulation is required at all. Thus, once attached to IV tubing lines, the tags of the present disclosure enable the user to quickly identify which IV solution is flowing through a which IV tubing line and to quickly differentiate various IV tubing lines from one another. Additionally, the fact that the user is able to view the liquid IV solution flowing through the IV tubing line enhances patient safety by enabling the user to determine whether there are any problems, such as blockages, within the section of the IV tubing line substantially surrounded by the IV tubing line attacher and the IV tubing line adhesive. Further, since the tags include the IV solution name pre-printed on one or more of their surfaces, users do not have to waste valuable time writing information on the tags prior to attaching them to the IV tubing lines. Rather, users simply detach a pre-printed tag from the safety device, remove the IV tubing line adhesive protective cover, and attach the tag to an IV tubing line.

Figure 9:
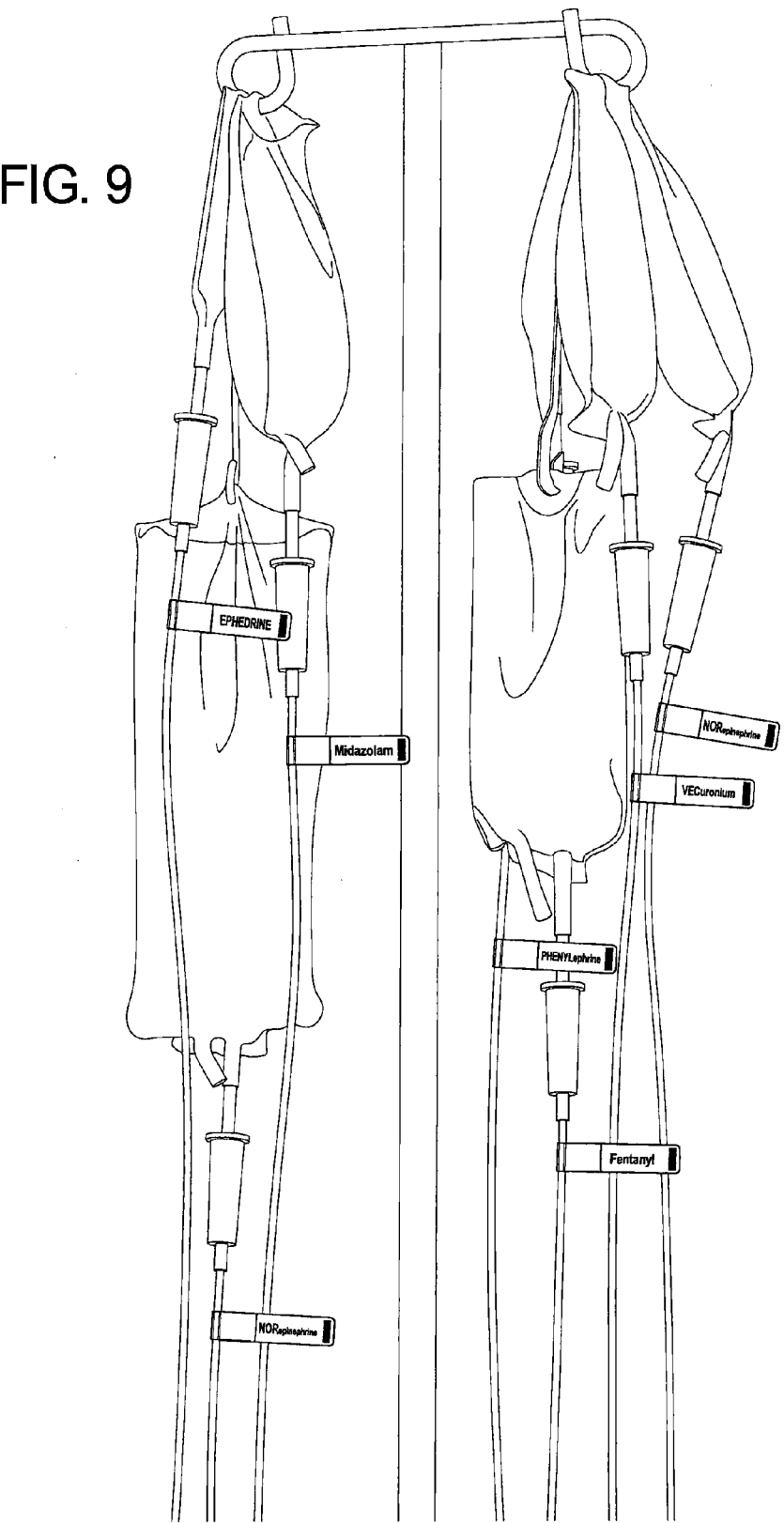
FIG. 9 is a front view of a plurality of IV bags and corresponding IV tubing lines each having a different tag from a different one of the IV bag/line safety devices of the present disclosure attached thereto.

FIG. 9 is a front view of a plurality of IV bags and corresponding IV tubing lines each having a different tag from a different one of the IV bag/line safety devices of the present disclosure attached thereto. It should be appreciated from this illustration that the use of the tags of the present disclosure enables a user to quickly and easily differentiate individual IV tubing lines from a plurality of IV tubing lines and identify which IV solution is flowing through which IV tubing line.

Once the tag is attached to the IV tubing line, it should be appreciated that none of the IV tubing line adhesive leaches into the IV tubing line and none of the ink printed on any components of the tag bleeds or smears. That is, the liquid IV solution flowing through the IV tubing line is not contaminated by the tag or any components thereof when the tag is attached to the IV tubing line, and the tag is waterproof.

In some embodiments in which the bag preparer (such as the IV bag manufacturer) attaches the safety device to the IV bag before sterilization, additional tags not physically attached to the safety device are sealed within the outer bag with the IV bag with the safety device attached thereto, the IV tubing line, and the IV solution contained therein. This enables a user to employ additional tags if the user so desires.

In certain embodiments, the tags are repositionable. That is, in these embodiments, after a user attaches a tag to an IV tubing line via the IV tubing line adhesive, the user may remove the tag from the IV tubing line and reattach the tag to the IV tubing line at another (such as a more desirable) location. To do so, the user peels the IV tubing line attacher off of the back surface of the IV solution name displayer and the IV tubing line, which releases the tag from the IV tubing line and enables the user to reattach the tag elsewhere as described above.

Materials

In one embodiment, the head, the neck, the first IV solution name displayer, the first IV tubing line adhesive protective cover, the second IV solution name displayer, the second IV tubing line adhesive protective cover, the third IV solution name displayer, and the third IV tubing line adhesive protective cover are each high quality laser printable synthetic paper made from 7 milliinch rigid polyester. The 7 milliinch rigid polyester features a bright white toner receptive coating on both sides designed for: (a) color laser printing, (b) Xeikon digital printing, (c) flexographic printing, (d) offset lithographic printing, (e) screen printing, and (f) thermal transfer printing. Properties of the 7 milliinch rigid polyester are included in Table 1 below.

TABLE 1

Properties of 7 Milliinch Rigid Polyester

| Property | Units | Value | Test Method |
| --- | --- | --- | --- |
| Nominal Gauge - Average | Milliinches | 7.0 | Continuous Gauging |
|  | Microns | 178 |  |
| Coefficient of Friction |  |  |  |
| Static | — | 0.73 | ASTM D-1894 |
| Kinetic | — | 0.561 |  |
| Tensile Strength |  |  |  |
| Machine Direction | PSI | 22,600 | ASTM D-882 |
| Transverse Direction | PSI | 23,100 |  |
| Elongation |  |  |  |
| Machine Direction | — | 119.0 | ASTM D-882 |
| Transverse Direction | — | 197.6 |  |

TABLE 1-continued

Properties of 7 Milliinch Rigid Polyester

| Property | Units | Value | Test Method |
| --- | --- | --- | --- |
| Gloss | — | 4.1 | ASTM D-523 |
| Light Transmission | — | 14.7 | ASTM D-1003 |
| Heat Shrinkage |  |  |  |
| Machine Direction | — | 1.5 | ASTM D-1204 |
| Transverse Direction | — | 0.5 |  |
| FDA Status |  | None |  |

In another embodiment, the head, the neck, the first IV solution name displayer, the first IV tubing line adhesive protective cover, the second IV solution name displayer, the second IV tubing line adhesive protective cover, the third IV solution name displayer, and the third IV tubing line adhesive protective cover are each a matte-finish, calcium carbonate-filled, calendared polypropylene, such as Fasson Rapid-Roll 10 Mil Polyith GC-2. The Fasson Rapid-Roll 10 Mil Polyith GC-2 is print-friendly via flexographic, letterpress, and thermal transfer, and is FDA acceptable. Properties of the Fasson Rapid-Roll 10 Mil Polyith GC-2 are included in Table 2 below.

TABLE 2

Properties of the Fasson Rapid-Roll 10 Mil Polyith GC-2

| Property | Typical Value | Test Method |
| --- | --- | --- |
| Basis Weight | 200.0 lbs/ream | T410A (500 sheets 25' × 38') |
| Caliper | 10.0 mils | T411 |
| Yield | 2.369 msi/lb | ASTM D 4321 |
| Tear | 550.0 MD/630.0 CD grams | T414 Elmendorf |
| Tensile | 4,000.0 MD/2,500.0 CD lbs/in | T494 |
| Opacity | 92.0% | T425 |
| Flexural Modulus of Elasticity | 180,000 psi | — |

It should be appreciated that the head, the neck, the first IV solution name displayer, the first IV tubing line adhesive protective cover, the second IV solution name displayer, the second IV tubing line adhesive protective cover, the third IV solution name displayer, and the third IV tubing line adhesive protective cover may be any suitable material.

In one embodiment, the first IV tubing line attacher, the second IV tubing line attacher, and the third IV tubing line attacher are each 2.2 milliinch clear gloss top coated polypropylene face material. Properties of the 2.2 milliinch clear gloss top coated polypropylene are included in Table 3 below.

TABLE 3

Properties of the 2.2 Milliinch Clear Gloss Top Coated Polypropylene

| Chemical Resistance | |
| --- | --- |
| Distilled Wager (24 hr) | No Effect |
| Detergent (24 hr) | No Effect |
| 10% HCl (10 min) | No Effect |
| 10% Ammonium Hydroxide (10 min) | No Effect |
| Anti-Freeze (24 hr) | No Effect |
| FDA Status Approved | |
| Code of Federal Regulations - Title 21: Food and Drugs 175.105 - Adhesives | |

In another embodiment, the first IV tubing line attacher, the second IV tubing line attacher, and the third IV tubing line attacher are each 2.0 mil clear top coated polypropylene film, such as MACtac PF9002-78 Vivid 2 Clear Polypropylene or MACtac PF9502-78 Vivid 2 Clear Polypropylene. Properties of the MACtac PF9002-78 and PF9502-78 are included in Table 4 below.

TABLE 4

Properties of the MACtac PF9002-78 and PF9502-78

| Property | Value | Test Method |
| --- | --- | --- |
| Caliper, inches | 0.002 (2 mil) | ASTM D2103 |
| Elongation, % (YIELD) | 12 MD 48 CD | ASTM D882 |
| Tensile, lbs./in. (YIELD) | 15 MD 68 CD | ASTM D882 |

It should be appreciated that the first IV tubing line attacher, the second IV tubing line attacher, and the third IV tubing line attacher may be any suitable material.

In one embodiment, the first IV tubing line adhesive, the second IV tubing line adhesive, the third IV tubing line adhesive, and the bag attacher adhesive are each a 1 milliinch medium-peel removable acrylic adhesive. Properties of the 1 milliinch medium-peel removable acrylic adhesive are included in Table 5 below.

TABLE 5

Properties of the 1 Milliinch Medium-Peel Removable Acrylic Adhesive

| Typical Characteristics | | |
| --- | --- | --- |
| Target Adhesion Values (PSTC-1, 180° peel @ 12'/min., 73° F., on Stainless Steel) | 15 min. 20 oz. | 24 hr. 25 oz. |
| Minimum Application Temperature | 50° F. | |
| Service Temperature Range | −40° F. to +180° F. | |
| Shelf Life (@ 73° F., 50% RH) | 2 years | |
| Chemical Resistance | | |
| Distilled Wager (24 hr) | No Effect | |
| Detergent (24 hr) | No Effect | |
| 10% HCl (10 min) | No Effect | |
| 10% Ammonium Hydroxide (10 min) | No Effect | |
| Anti-Freeze (24 hr) | No Effect | |
| SAE 20 Motor Oil (24 hr) | No Effect | |
| Gasoline (1 hr) | No Effect | |
| FDA Status Approved | | |
| Code of Federal Regulations - Title 21: Food and Drugs 175.105 - Adhesives | | |

In another embodiment, the first IV tubing line adhesive, the second IV tubing line adhesive, the third IV tubing line adhesive, and the bag attacher adhesive are each MACtac 710VHP adhesive. The MACtac 710VHP adhesive is a rubber-based adhesive capable of adhering to a variety of surfaces including polystyrene, polypropylene, polyethylene, paper, and corrugate. The MACtac 710VHP adhesive is compliant with FDA 21 C.F.R. 175.105. Properties of the MACtac 710VHP adhesive are included in Table 6 below.

TABLE 6

Properties of the MACtac 710VHP Adhesive

| Property | Value | Test Method |
| --- | --- | --- |
| Thickness, inches | 0.0007 +/− 10% (0.7 mil) | — |

TABLE 6-continued

Properties of the MACtac 710VHP Adhesive

| Property | Value | Test Method |
| --- | --- | --- |
| Peel Adhesion, lbs./in. | Corrugate: 1.3 HDPE: 1.8 Stainless Steel: 2.7 | PSTC-1 (30 min applied) |
| Loop Tack (1'), lbs./in. | Corrugate: 2.3 HDPE: 3.2 Stainless Steel: 4.8 | CTM-25 |
| Minimum Application Temperature | +20° F. (−7° C.) | CTM #45 Curwood Polyester Film Dry Surface |
| Service Range Temperature | −65° F. to +160° F. (−54° C. to +71° C.) | CMT #45 Curwood Polyester Film Dry Surface |

In another embodiment, the first IV tubing line adhesive, the second IV tubing line adhesive, the third IV tubing line adhesive, and the bag attacher adhesive are each MACtac TM1039 adhesive. The MACtac TM1039 adhesive is a 3 mil thick transfer film of high performance, synthetic rubber based adhesive. The MACtac TM1039 adhesive is in accordance with ISO 10993-5/-10 standards, and bonds to a wide variety of materials including low energy surfaces such as polyethylene and polypropylene. The MACtac TM1039 adhesive also provides the mass needed to establish secure bonds to uneven or irregular surfaces. The MACtac TM1039 adhesive is free of natural rubber latex. Properties of the MACtac TM1039 adhesive are included in Table 7 below.

TABLE 7

Properties of the MACtac TM1039 Adhesive

| Property | Value | Test Method |
| --- | --- | --- |
| Quick Tack, lbs./sq. in., Stainless Steel | 12.0 | MACtac CTM-25 |
| Peel Adhesion, lbs./in., Stainless Steel - 30 min. residence | 11.0 | PSTC-3 |
| Shear, hours to fail, Stainless Steel - 1000 g/sq. in. @ 72° F. | 300+ | PSTC-7 |
| Thickness, inches, Adhesive only | 0.003 (3 mil) | — |
| Minimum Application Temperature | Above 50° F. (10° C.) for best performance | — |
| End Use Temperature Range | 0° F. to 180° F. (−18° C. to 82° C.) | |

In another embodiment, the first IV tubing line adhesive, the second IV tubing line adhesive, the third IV tubing line adhesive, and the bag attacher adhesive are each MACtac ST95 adhesive. The MACtac ST95 adhesive is an acrylic emulsion. The MACtac ST95 adhesive has very good adhesion to corrugated, glass, and various plastic substrates, and is latex glove friendly for use in healthcare applications. The MACtac ST95 adhesive complies with FDS 21 C.F.R. 175.105. Properties of the MACtac ST95 adhesive are included in Table 8 below.

TABLE 8

Properties of the MACtac ST95 Adhesive

| Property | Value | Test Method |
| --- | --- | --- |
| Thickness, inches | 0.0007 +/− 10% (0.7 mil) | — |

TABLE 8-continued

Properties of the MACtac ST95 Adhesive

| Property | Value | Test Method |
|---|---|---|
| Peel Adhesion, lbs./in. | 2.6 | PSTC-1 (30 min applied) |
| Minimum Application Temperature | +25° F. (−4° C.) | CTM #45 Curwood Polyester Film Dry Surface |
| Service Range Temperature | −75° F. to +200° F. (−59° C. to +93° C.) | CTM #45 Curwood Polyester Film Dry Surface |

It should be appreciated that the first IV tubing line adhesive, the second IV tubing line adhesive, the third IV tubing line adhesive, and the bag attacher adhesive may be any suitable adhesive. In one embodiment, each of first IV tubing line adhesive, the second IV tubing line adhesive, the third IV tubing line adhesive, and the bag attacher adhesive are the same adhesive. In another embodiment, at least two of the first IV tubing line adhesive, the second IV tubing line adhesive, the third IV tubing line adhesive, and the bag attacher adhesive are different adhesives. For example, in one embodiment, The first IV tubing line adhesive, the second IV tubing line adhesive, and the third IV tubing line adhesive are the MACtac ST-95 adhesive and the bag attacher adhesive is the MACtac 710VHP adhesive.

In one embodiment, the release coating is a curable polymer coating, such as Corkure 1093RHG-45. The Corkure 1093RHG-45 is an epoxy acrylate based overprint varnish that is 100% reactive and contains no solvents. The Corkure 1093RHG-45 has a high gloss, cures quickly, and is flexible and foldable. The Corkure 1093RHG-45 includes trimethylolpropane triacrylate (25-35% by weight), tripropylene glycol diacrylate (20-30% by weight), reactive tertiaryamine (5-15% by weight), and acrylate ester of bisphenol epoxy (20-30% by weight). Properties of the Corkure 1093RHG-45 are included in Table 8 below.

TABLE 9

Properties of the Corkure 1093RHG-45

| Property | Value |
|---|---|
| Viscosity | 80-105 cps |
| Solids | 100% |
| Cure Rate | 150 fpm/300 W |
| Rub Resist | +200 rubs/4 lb. weight |
| Specific Gravity | 1.07-1.08 g/cm$^3$ |
| Gloss @ 60° | 90 or greater |
| pH | 7.2-9.0 |
| Adhesion | Excellent |

It should be appreciated that the release coating may be any suitable coating.

In one embodiment, the bag attacher adhesive liner is 60# white kraft paper liner. Properties of the 60# white kraft paper liner are included in Table 10 below.

TABLE 10

Properties of the 60# White Kraft Paper Liner

| Chemical Resistance | |
|---|---|
| Distilled Wager (24 hr) | No Effect |
| Detergent (24 hr) | No Effect |
| 10% HCl (10 min) | No Effect |
| 10% Ammonium Hydroxide (10 min) | No Effect |
| Anti-Freeze (24 hr) | No Effect |

TABLE 10-continued

Properties of the 60# White Kraft Paper Liner

| | |
|---|---|
| SAE 20 Motor Oil (24 hr) | No Effect |
| Gasoline (1 hr) | No Effect |
| FDA Status Approved | |
| Code of Federal Regulations - Title 21: Food and Drugs 175.105 - Adhesives | |

In another embodiment, the bag attacher adhesive liner is a semi-bleached calendared kraft liner. Properties of the semi-bleached calendared kraft liner are included in Table 11 below.

TABLE 11

Properties of Semi-Bleached Calendared Kraft Liner

| Property | Value | Test Method |
|---|---|---|
| Caliper, inches | 0.00245 +/− 10% (2.45 mil) | TAPPI T-411 |
| Basis Weight, lbs. (24' × 36'/500 sheets) | 40 +/− 10% | TAPPI T-410 |

It should be appreciated that the bag attacher adhesive liner may be any suitable material.

In one embodiment, the IV solution names and the barcodes are printed on the IV solution name displayers using a black, FDA approved UV Flexo Ink such as ACTEGA WIT PharmaFlex high definition UV curable flexographic printing ink. In one embodiment, the UV Flexo Ink has a neutral pH and a density of 9.18 lb/gal.

Method of Manufacturing

The safety device of the present disclosure may be manufactured in any of a variety of different manners. In one embodiment, the safety device is manufactured as follows. An IV solution name is printed at three different areas on both the front and back surfaces of Fasson Rapid-Roll 10 Mil Polyith GC-2 sheetstock. These printed areas of the sheet of polyester will, upon completion of production, become the IV solution name displayers. The first tag perforated edge, the second tag perforated edge, and the third tag perforated edge are cut. MACtac PF9502-78 Vivid 2 Clear Polypropylene is attached to a portion of the top surface of the Fasson Rapid-Roll 10 Mil Polyith GC-2 sheetstock using MACtac ST95 adhesive. A semi-bleached calendared kraft liner is attached to an area of the back surface of the Fasson Rapid-Roll 10 Mil Polyith GC-2 sheetstock using MACtac 710VHP adhesive. The outline (i.e., the outer edges) of the safety device and the first perforated edge, the second perforated edge, and the third perforated edge are cut. It should be appreciated that the safety device is manufactured so as to minimize waste of materials.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An intravenous bag/line safety device for an IV bag with a hanger hole comprising:

a bag attacher including:
(a) a head for insertion through the hanger hole of the IV bag,
(b) a neck connected to the head,
(c) a bag attacher adhesive disposed on one surface of at least one of the head and the neck, and
(d) an adhesive liner removably attached to the bag attacher adhesive; and
a tag set connected to the bag attacher, the tag set including a plurality of intravenous tubing line safety tags each having an intravenous solution name displayer with two opposed surfaces displaying the name of a pharmaceutical or solution on each of the two surfaces and an adhesive-bearing IV tubing line attacher.

2. The intravenous bag/line safety device of claim 1, wherein the tag set is removably connected to the bag attacher via a perforated line between the neck and at least one of the intravenous tubing line safety tags.

3. The intravenous bag/line safety device of claim 1, wherein the intravenous tubing line attacher is substantially transparent.

4. The intravenous bag/line safety device of claim 1, wherein at least one of the intravenous tubing line safety tags is removably connected to at least one other one of the intravenous tubing line safety tags.

5. The intravenous bag/line safety device of claim 1 in which the intravenous tubing line safety tags include:
(i) an intravenous solution name displayer removably connected to an intravenous tubing line adhesive protective cover, the intravenous solution name displayer displaying a name of a pharmaceutical; and
(ii) an intravenous tubing line attacher having an intravenous tubing line adhesive disposed on one surface of the intravenous tubing line attacher.

6. The intravenous bag/line safety device of claim 5 in which the intravenous tubing line adhesive protective cover and a portion of the intravenous solution name displayer are removably attached to the intravenous tubing line adhesive.

7. The intravenous bag/line safety device of claim 6, in which each of the intravenous tubing line safety tags is removably connected to at least one other one of the intravenous tubing line safety tags.

8. The intravenous bag/line safety device of claim 1 in which the bag attacher is sterile.

9. The intravenous bag/line safety device of claim 1 in which at least one safety tag includes an RFID.

10. The intravenous bag/line safety device of claim 1 in which the tubing line safety tags are rigid.

11. The intravenous bag/line safety device of claim 1 in which the bag attacher adhesive is disposed on surfaces of both the head and the neck of the bag attacher.

12. An intravenous bag/line safety device for an IV bag with a hanger hole comprising:
a bag attacher attachable to an intravenous bag, the bag attacher including a head for insertion through the hanger hole of the IV bag and a bag attacher adhesive disposed on one surface of the head; and
a tag set including a plurality of intravenous tubing line safety tags configured to be attached to an intravenous tubing line to identify a pharmaceutical included in an intravenous solution to be delivered from an intravenous bag to which the bag attacher is removably connected, wherein each of the intravenous tubing line safety tags is also individually removably connected to the tag set, and wherein the bag attacher and the tag set are in addition to any permanent labels on the intravenous bag.

13. The intravenous bag/line safety device of claim 12, wherein the bag attacher includes a bag attacher and a bag attacher adhesive liner removably attached to and covering the bag attacher adhesive.

14. The intravenous bag/line safety device of claim 12, wherein the intravenous tubing line safety tags include:
(a) an intravenous solution name displayer removably connected to an intravenous tubing line adhesive protective cover, the intravenous solution name displayer displaying a name of the pharmaceutical; and
(b) an intravenous tubing line attacher having an intravenous tubing line adhesive disposed on one surface of the intravenous tubing line attacher, wherein the intravenous tubing line adhesive protective cover and a portion of the intravenous solution name displayer are removably attached to the intravenous tubing line adhesive.

15. The intravenous bag/line safety device of claim 12, wherein at least one of the intravenous tubing line safety tags is removably connected to at least one other intravenous tubing line safety tag.

16. An intravenous bag adapted for improved intravenous line marking comprising:
an intravenous bag containing an intravenous solution having a hanger hole; and
an intravenous bag/line safety device attached to the intravenous bag, the intravenous bag/line safety device including:
(a) a bag attacher including a bag attacher adhesive attached to the intravenous bag; and
(b) a tag set connected to the bag attacher and hanging free of the intravenous bag, the tag set including a plurality of intravenous tubing line safety tags, wherein the intravenous tubing line safety tags are:
(i) removably connected to the tag set,
(ii) attachable to an intravenous tubing line, and
(iii) configured to identify the pharmaceutical, the intravenous bag/line safety device having:
(a) a head positioned on one side of the hanger hole,
(b) a neck connected to the head and extending away from the opposite side of the hanger hole,
(c) the bag attacher adhesive disposed on at least one surface of the head and the neck, and
(d) a bag attacher adhesive liner removably attached to and covering the bag attacher adhesive.

17. The apparatus of claim 16, wherein the intravenous tubing line safety tags include:
(a) an intravenous solution name displayer removably connected to an intravenous tubing line adhesive protective cover, the intravenous solution name displayer displaying a name of the pharmaceutical; and
(b) a substantially transparent intravenous tubing line attacher having an intravenous tubing line adhesive disposed on one surface of the intravenous tubing line attacher, wherein the intravenous tubing line adhesive protective cover and a portion of the intravenous solution name displayer are removably attached to the intravenous tubing line adhesive.

18. The apparatus of claim 16, wherein each of the intravenous tubing line safety tags is removably connected to at least one other one of the intravenous tubing line safety tags.

19. The apparatus of claim 16, wherein an intravenous tubing line is connected to the intravenous bag, and one of the plurality of intravenous tubing line safety tags is attached to the intravenous tubing line.

* * * * *